United States Patent [19]
Dobrogosz et al.

[11] Patent Number: 5,352,586
[45] Date of Patent: Oct. 4, 1994

[54] **METHOD OF DETERMINING THE PRESENCE OF AN ANTIBIOTIC PRODUCED BY *LACTOBACILLUS REUTERI***

[75] Inventors: Walter J. Dobrogosz, Raleigh, N.C.; Sven E. Lindgren, Uppsala, Sweden

[73] Assignee: Biogaia AB, Stockholm, Sweden

[21] Appl. No.: 670,960

[22] Filed: Mar. 18, 1991

Related U.S. Application Data

[60] Division of Ser. No. 268,361, Sep. 19, 1988, abandoned, which is a continuation-in-part of Ser. No. 102,830, Sep. 22, 1987, abandoned, which is a continuation-in-part of Ser. No. 46,027, May 1, 1987, abandoned.

[51] Int. Cl.$^5$ .................. C12Q 1/04; C12P 17/08; C12N 1/20
[52] U.S. Cl. ..................... 435/34; 435/124; 435/252.1; 435/853; 435/183; 435/41
[58] Field of Search .............. 435/34, 124, 252.1, 435/853, 183, 41; 514/693

[56] References Cited

U.S. PATENT DOCUMENTS 3,689,640  9/1972  Shahani ............................. 424/118
4,048,299  9/1977  Litchfield .......................... 424/49

FOREIGN PATENT DOCUMENTS 190707  9/1985  Japan .
275217  12/1986  Japan .

OTHER PUBLICATIONS

Hall, R. H. et al., Acid-catalysed Hydration of Acraldehyde, J. Chem. Soc. 1950:490–498.
Hamden, I. Y. et al., Acidolin: An Antibiotic Produced by *Lactobacillus acidophilus*, J. Antibiotics 27:631–636, 1974.
Merck Index, Tenth Ed., 1983 pp. 5138.
Nielsen, A. et al., $^{13}$C and $^1$H NMR Study of Formaldehyde Reactions with Acetaldehyde and Acrolein, Pol. J. Chem. 55:1293–1403, 1981.
Pelczar et al., Phage-Typing in Laboratory Exercises in Microbiology, p. 207, 1977.
Reed, G., Starter Cultures for Fermented Dairy Products, in *Biotechnology*, vol. 5, 1983.
Sandine, W. E. et al., Lactic Acid Bacteria in Food and Health: A Review with Special Reference to Enteropathogenic *Escherichia coli* as Well as Certain Enteric Diseases and Their Treatment with Antibiotics and Lactobacilli, J. Milk Food Technol. 5:691–702, 1972.
Sarra, P. G. et al., Study on Crop Adhesion Determinant in *Lactobacillus reuteri*, Microbiologica 9:279–285, 1986.
Shahani, K. M. et al., Natural Antibiotic Activity of *Lactobacillus Acidophilus* and *Bulgaricus*, Cult. Dairy Prod. J. 12:8–11, 1977.
Sobolov, et al., Metabolism of Glycerol by an Acrolein-Forming Lactobacillus, J. Bacteriol. 79:261–266, 1960.
Talarico, T. L. et al., Production and Isolation of Reuterin, a Growth Inhibitor Produced by *Lactobacillus reuteri*, Antimicrobial Agents and Chemother., 32:1854–1858, 1988.
Vescovo. M. et al., Drug Resistance Plasmids in *Lactobacillus acidophilus* and *Lactobacillus reuteri*, Appl. Environ. Microbiol. 43:50–56, 1982.
Gerhardt et al, Manual of Methods for General Bacteriology, 1981, p.120.

*Primary Examiner*—Irene Marx
*Attorney, Agent, or Firm*—Olive & Olive

[57] ABSTRACT

The antibiotic reuterin is obtained by cultivating strains of *Lactobacillus reuteri* under controlled conditions. Reuterin has inhibitory activity against Gram positive and Gram negative bacteria, against yeast, *Saccharomyces cerevisiae*, and against the protozoan, *Trypanosoma cruzi*. Reuterin producing strains are identified by grown inhibition of susceptible microorganisms in the presence of glycerol or glyceraldehyde.

4 Claims, 17 Drawing Sheets

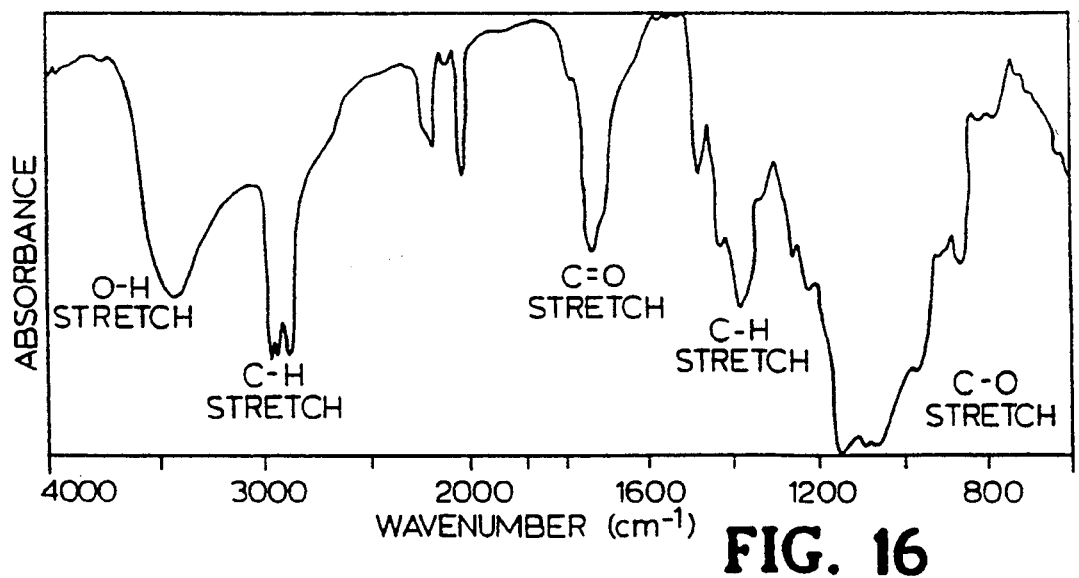
FIG. 16
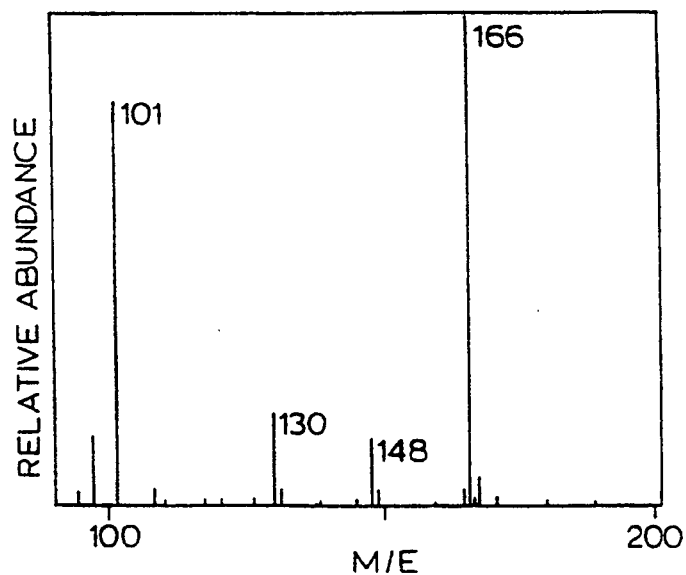
FIG. 17
FIG. 20
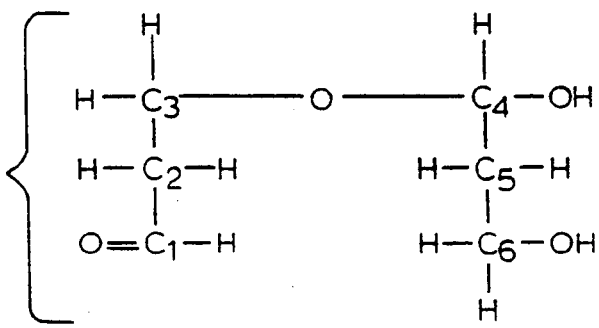

REUTERIN

METHOD OF DETERMINING THE PRESENCE OF AN ANTIBIOTIC PRODUCED BY *LACTOBACILLUS REUTERI*

This is a divisional application of Ser. No. 07/268,361, filed Sep. 19, 1988, now abandoned, which is a continuation-in-part of Ser. No. 07/102,830 filed Sep. 22, 1987, (now abandoned) which is a continuation-in-part of Ser. No. 07/046,027, filed May 1, 1987, (now abandoned).

FIELD OF THE INVENTION

This invention relates to a new antibiotic designated reuterin, procedures for isolating and cultivating reuterin-producing strains of *Lactobacillus reuteri* from animal sources, and procedures for isolation and purification of reuterin.

BACKGROUND INFORMATION

*Lactobacillus reuteri*, a newly designated species of Lactobacillus (some strains of this species were previously identified as *Lactobacillus fermentum* (1, 2)), is a symbiotic resident of the gastrointestinal (GI) tracts of humans, swine and other animals. The neotype strain of *L. reuteri* is DSM 20016 (ATCC No. 53609). This strain and the newly isolated strain 1063 (ATCC No. 53608) are available to the public at the American Type Culture Collection (Rockville, Md.) having been deposited therein under The Budapest Treaty Apr. 17, 1987. The GI tract of animals is a complex ecosystem harboring an estimated 300–500 species of microorganisms, known collectively as the indigenous microbiota. Despite over 100 years of intensive research in the field of intestinal microbiology much remains to be learned about these microorganisms, the complex interrelationships that exist between the different species and the nature of the symbiotic relationships existent between the microbiota and their host.

Under certain conditions some members of the indigenous microbiota can become opportunistic pathogens causing a variety of enteric diseases. More often, however, pathogens gain access to the GI tract as contaminants in food or water. Notable among the latter are a number of bacteria (e.g., *Escherichia coli*, Salmonella species, Shigella species, *Yersina intercolitica*, *Vibrio cholera*, *Vibrio parahaemolyticus*, *Campylobacter jejuni* and *Clostridium difficile*), viruses (e.g., roto-, astro- and ciliciviruses) and intestional parasites (e.g. Giardia and Entamoeba species). Acute and chronic enteric diseases caused by these and other microorganisms occur worldwide causing considerable human misery and loss of economically important animals. Certain microbial activities have also been associated with production of mutagens within the GI tract.

It is also known that the indigenous microbiota exist in a symbiotic or synergistic relationship with their host contributing in many positive (probiotic) ways to the host's general health and well-being. It is well-known that germ-free animals are not particularly healthy and have poorly developed GI tracts. In return for the nutrient-rich and stable ecosystem provided for the, the indigenous microbiota provide their hosts with an assortment of benefits including among others (i) protection against enteric pathogens, (ii) stimulation of normal development and function of the GI epithelial mucosal system, (iv) production of various vitamins and other nutrients and (v) remetabolism of the host's abundant endogenous mucosal tissue.

At the present time there is little understanding of how the composition and numbers of the indigenous microbiota are controlled. It is viewed that these controls are the consequences of complex interactions among the numerous species involving such factors as: redox potential, surface pH, inhibitory effects of fatty acids, hydrogen sulfide, deconjugated bile salts and as yet unidentified inhibitory substances, as well as factors such as competition for limiting nutrients and the ability of the microbiota to associate with and adhere to the epithelial surfaces of the GI tract.

Shortly after birth of an animal, *Escherichia coli* and enteric streptocci are almost universally the first bacteria to appear in the GI tract. The lactobacilli almost always accompany or immediately follow in sequence and become a dominant bacterial group found in the intestines. It is viewed that the small intestine microroganisms, particularly those belonging to the Lactobacillus and Streptococcus genera, have protective value against bacterial and non-bacterial pathogens and promote healthy weight gains in animals. Being among the more nutritionally fastidious of the enteric microbiota, the lactobacilli are believed to find their ecological niche in the more proximal, nutrient rich regions rather than in the distal regions of the GI tract.

It has been reported on numerous occasions that the lactobacilli (3), which include a large number of non-pathogenic, non-toxic bacteria, play an important probiotic role in the health and well-being of humans and animals. Lactobacillus species are added to human and animal foodstuffs to preserve them, enhance their flavors and/or for probiotic purposes so that these bacteria will become available to the GI tract. *Lactobacillus plantarum* strains, for example, are grown commercially in large amounts and used as starter cultures for the commercial preservation of a variety of human (meats, vegetables and dairy products) and animal (silage) foods. *Lactobacillus acidophilus* strains are grown commercially in large amounts to be added to human (e.g., milk) or animal (feedstuffs) foods as a means of introducing these bacteria into the GI tract for probiotic benefits. Reports on the beneficial effects of Lactobacillus therapy have increased in recent years with findings that dietary Lactobacillus therapy (i) affords protection from colon cancer for human populations on western diets (4), (ii) reduces the incidence of experimentally induced large bowel tumors in rats (5), (iii) reduces the fecal concentration of bacterial enzymes known to catalyze the conversion of pro carcinogens to proximal carcinogens in humans (6), and (iv) reduces the serum cholesterol levels in swine (7).

The metabolic endproducts of Lactobacillus metabolism such as acetic acid, lactic acid and hydrogen peroxide are well-known for their antimicrobial activities. Two laboratories have reported that the heterofermentative species *Lactobacillus brevis*, *Lactobacillus buchneri* (8) and Lactobacillus strain 208-A (9,10) metabolize glycerol anaerobically. The latter strain carries out an anaerobic dehydration (involving glycerol dehydratase) of 2 moles of glycerol yielding 2 moles of β-hydroxypropionaldehyde which in turn is dismutated to 1 mole of β-hydroxypropionic acid and 1 mole of 1,3-propanediol. Some lactobacilli also produce bacteriocins or baceteriocin-like proteins which exhibit bacteriocidal activity toward other members of that species or closely related species. Some unconfirmed reports have appeared concerning low molecular weight, antimicrobial substances produced by lactobacilli. Although their existence has been predicted for some time, such substances have not been confirmed or isolated.

Following is a summary of what is known concerning antimicrobial activities associated with lactobacilli. In 1907, Metchnikoff (11) proposed that harmful putrefying bacteria residing in the GI tract were inhibited (or antagonized) by acid-producing lactobacilli. Since then a variety of such antagonistic activities associated with lactic acid bacteria have been reported (12). Most often these antimicrobial activities have been found to be associated with major end products of metabolism such as lactic and acetic acids and hydrogen peroxide (13–18). Other reports have appeared concerning antimicrobial activities associated with lactobacilli but not associated with these normal end products of metabolism. Gilliland and Speck (19) reported a broad-spectrum antagonism which varied among different *Lactobacillus acidophilus* strains tested. Hydrogen peroxide was partially responsible for the inhibitory response. Tramaer (20) showed that *L. acidophilus* inhibition of *E. coli* was due to the strong germicidal action of lactic acid at low pH. Formation of an additional inhibitor also was suggested but not identified. Broad spectrum antagonistic substances also have been reported by Shahani et al., Reddy and Shahani, and Hamdan and Mikolagcik (21–25). In each of these reports, the antagonistic substances were produced during Lactobacillus growth in 11% non-fat, dry milk solids and were difficult to distinguish from lactic acid and thus appear to be totally unrelated to reuterin. Of these studies Hamdan and Mikolagcik (24–25) performed the most intensive purification and characterization of the substance they termed acidolin. They found it to be a low molecular weight (approximately 200) compound, free of nitrogen, acidic in nature, and extremely heat resistant. The conditions under which this substance is produced and its acidic nature clearly distinguish it from reuterin. A survey for antagonistic activities among yogurt cultures (26) could not identify inhibitory substances other than lactic acid in strains of *L. acidophilus, L. bulgaricus, L. casei, L. helveticus,* and *L. lactis.* One of the *L. bulgaricus* strains tested had been reported previously to produce an antibiotic termed bulgarican (23).

A number of lactobacilli are known to produce bacteriocins which are proteins exhibiting bacteriocidal activities. Most bacteriocins of bacteriocin-like substances produced by lactobacilli exhibit a narrow range of biological activity. Vincent et al. (27) however reported a broad-spectrum bacteriocin, termed lactocidin, produced by a number of *L. acidophilus* isolates. No other reports of broad-spectrum bacteriocins produced by lactobacilli have been reported (12). Bacteriocins are polypeptides and their inhibitory properties are destroyed by pro teases. Reuterin is not a polypeptide and its antimicrobial activity is unaffected by proteases.

In addition to their ability to produce certain antibiotic substances, Sandine (28) has proposed a number of roles or functions the lactobacilli could play in the human (and animal) intestinal tract. These include: organic acid production, lower pH and oxidation-reduction potential, competitive antagonists, bile deconjugation and carcinogen suppression. Dietary adjunct lactobacilli are deemed beneficial by providing disease therapy, preventative therapy and as a source of needed enzymes.

SUMMARY OF THE INVENTION

According to the present invention, biologically pure strains of *L. reuteri* are provided. Under the controlled cultivation methods of the invention, these strains produce a newly isolated and characterized broad-spectrum antimicrobial substance termed reuterin. This antibiotic may be used to kill other microorganisms under defined conditions using a microorganism (*L. reuteri*) that is nonpathogenic to humans and other animals. The technique of the invention for isolation of reuterin-producing *Lactobacillus reuteri* strains may also be used to isolate strains from humans and agriculturally important animals so that these isolated strains may be used as probiotic agents for the specific animal from which they were isolated. Thus, *L. reuteri* 1063, isolated from swine has potential use as a probiotic agent in moderating colibacillosis and weanling diarrheal disease in swine and for increasing their feed efficiencies. In comparison to a number of other homo- and heterofermentative lactobacillil isolated directly from swine small intestines, and also in comparison to *L. reuteri* strains 20016 and 27273 which have been held in stock culture for long periods of time, *L. reuteri* 1063 demonstrates strong auto-agglutination, a high degree of surface hydrophobicity and binds better than other strains to swine epithelial cells in culture. A process for the production of reuterin and a procedure for isolation of reuterin-producing strains of *L. reuteri* from the GI tract (or stools) of all animals harboring this species are also provided. Production of large quantities of a naturally occurring broad spectrum antibiotic as provided by the invention makes possible the use of this antibiotic for treatment of a variety of diseases and as a general purpose antimicrobial agent.

BRIEF DESCRIPTION OF THE DRAWINGS

FIG. 16 shows the Fourier Transform Infrared analysis of reuterin.

FIG. 17 shows the liquid chromatography/mass spectrometry analysis of reuterin.

FIG. 20 shows the proposed structure giving rise to the spectra of FIGS. 18 and 19.

Figure 1:
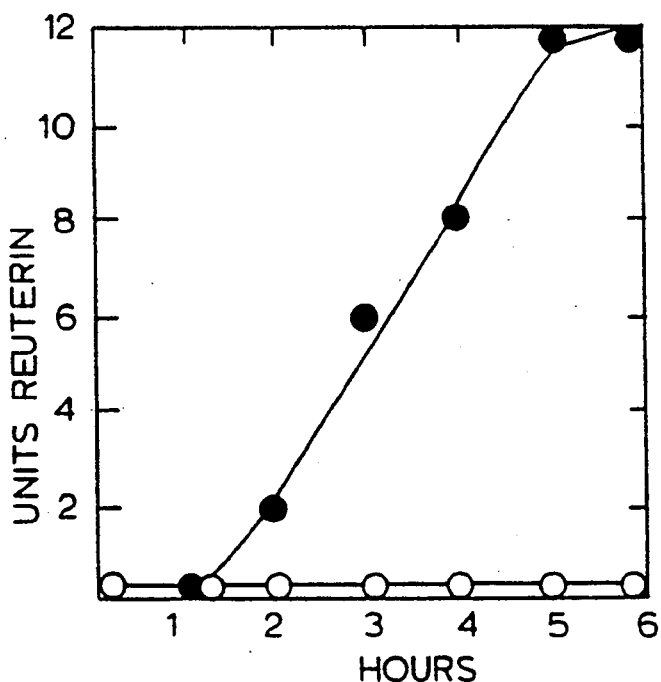
FIG. 1 shows production of reuterin under aerobic (shaking) and semi-anaerobic (still culture) conditions in a glycerol medium.

DESCRIPTION OF THE PREFERRED EMBODIMENTS AND EXAMPLES OF THE PREFERRED EMBODIMENTS

Isolation of Antibiotic-producing strains

Host-specific *Lactobacillus reuteri* strains may be isolated from an animal source such as the GI tract or stools of animals harboring the species by the methods of this invention. *L. reuteri* grows best under anaerobic conditions but will grow aerobically. Suspensions from the GI tract or stools are spread on agar plates of a medium suitable for Lactobacillus growth and the agar plates are incubated under conditions that promote growth of Lactobacillus colonies. In the preferred embodiment, well developed colonies appear on the surface of Lactobacillus Selection Medium (LBS) agar plates after 48 hours of anaerobic growth (reduced oxygen tension) at 37 degrees C. LBS Medium contains (g/L): Trypticase, 10; Yeast Extract, 5; $KH_2PO_4$, 61; ammonium citrate, 2; sodium acetate (tri-hydrate) 34; $MgSO_4$, (hepta-hydrate), 1.2; $MnSO_4$ (mono-hydrate), 0.13; $FeSO_4$ (hepta-hydrate), 0.06. The pH is adjusted to 5.5 with concentrated HCl; agar (25 g) is added. Glucose (10 g) is added after sterilization of the medium. Other Lactobacillus growth media may be used. In the preferred embodiment the LBS plates are overlayed with 10 ml of 1% liquified agar containing 0.50M glycerol and a *Lactobacillus plantarum* inoculum. To insure isolation of the respective reuterin-producing producing colonies, either replicate plates are prepared of all Lactobacillus colonies growing on the initial LBS plates prior to further testing, using LBS Medium or another Lactobacillus growth medium, or Lactobacillus cells are transferred by any other technique from each of the colonies on the LBS plates to a growth medium before adding the overlay (replication procedure). After this overlay has solidified the plates are against incubated at 37 degrees C. in anaerobic jars for 48 hr. Zones of growth inhibition of the seeded *L. plantarum* are observed around the colonies that produce the antibiotic, reuterin, under these conditions.

The identification of *L. reuteri* strains is confirmed using standard microbiological tests and the taxonomic characteristics of the species. *L. reuteri* is a heterofermentative species forming gas from glucose and gluconate and acetate/ethanol from glucose. In the API 50 CH fermentation test (Analytab Products, Sherwood Medical Co., New Brunswick, N.J.) it exhibits a positive reaction with ribose, arabinose, glucose, galactose, lactose, sucrose, melibiose and maltose (some strains also ferment xylose). The species has a quanine plus cytosine mol. % of 39–41, lysine is the murein diaminoacid and the species grows as 45 degrees but not 15 degrees C. Strains having 80% or higher DNA-DNA homology with neotype strain, DSM 20016, can be found in the GI tract of animals.

Using the methods of this invention, *Lactobacillus reuteri* strain 1063 has been isolated from the swine gastro-intestinal tract and has been shown (discussed below) to be capable of producing much higher levels of reuterin than the other strains tested. Strains 1063 and strain DSM 20016 have been deposited with the American Type Culture Collection, Rockville, Md., (ATCC Numbers 53608 and 53609, respectively (deposited Apr. 17, 1987).

The features and advantages of the present invention will be more clearly understood by reference to the following examples, which are not to be construed as limiting the invention.

EXAMPLES

Example I

Cultural Conditions for Production and Detection of Reuterin

When *Lactobacillus reuteri* cells capable of producing reuterin are placed under certain favorable conditions, reuterin is produced. A number of assays have been developed to detect and quantitate reuterin. A standard Minimum Inhibitory Concentration (MIC) procedure was adopted to detect reuterin and to elucidate factors affecting its production. *E. coli* K12 is used as the susceptible test microorganism and the assay is carried-out as follows. Overnight cultures of *E. coli* are harvested, washed twice with sterile 0.05 sodium phosphate buffer (pH 7.5), suspended in this buffer and adjusted to 60 percent transmission (A 420 nm) using a Spectronic 70 instrument. This suspension is diluted 1:100 and 0.1 ml aliquots are used to inoculate 1.0 ml of the MIC assay medium which contains (g/L): vitamin-free casein hydrolysate, 3; ammonium citrate, 1.9; citric acid, 0.63; $KH_2PO_4$, 12.6; $MgSO_4$ (hepta-hydrate), 0.2; pH adjusted to 7.0 and 20 mM glucose added after sterilization. Sterile 1.0 ml portions of samples to be tested for reuterin activity are added to 1.0 ml of this inoculated MIC assay medium and thoroughly mixed to obtain a 1:2 dilution. Such dilutions are continued in serial fashion as needed. These cultures are then incubated for 24 hours at 37 degrees C. and examined for growth. Relative reuterin concentrations (units reuterin) are then calculated as the reciprocal of the sample dilution preceding the dilution allowing visible growth of the indicator cells. Another assay relating MIC values to reuterin peak heights as determined by HPLC analyses (described below) has also been developed.

Under the conditions of the method of the invention *L. reuteri* produces the antimicrobial substance of the invention termed reuterin. A number of heterofermentative and homofermentative Lactobacillus strains have been tested for reuterin productions, and none, except *L. reuteri*, produce reuterin.

Conditions under which reuterin is produced have been determined. Reuterin is not produced under aerobic conditions (atmospheric oxygen concentration) but under reduced oxygen tension. It is produced when *L. reuteri* is cultured anaerobically (or semi-anaerobically in still culture) in the MIC assay medium described above containing 20–500 mM glycerol or glyceraldehyde in place of glucose as the major carbon and energy source. FIG. 1 shows production of reuterin under aerobic (curve 1) and semi-anaerobic (curve 2) conditions in this glycerol medium. *L. reuteri* does not grow under these conditions but nevertheless produces reuterin. Twenty other substances, including hexoses, hexitols, pentoses, pentitols, disaccharides and a variety of phosphorylated and non-phosphorylated $C_3$-substances, were tested for their ability to support reuterin production. Table 1 shows the results of some of these tests. The medium, containing a substrate at 20 mM ($C_6$ and $C_5$ substrates) or 40 mM ($C_3$ substrates) concentrations, was inoculated with $5 \times 10^6$ colony-forming units (CFU) per ml *E. coli* with and without *L. reuteri*. Only glycerol and glyceraldehyde yielded reuterin. Also, reuterin production from glycerol is inhibited when glucose or another growth substrate is included in the production medium. The results shown in Table 2 indicate the percent inhibition in viable count of a $6.7 \times 10^7$ CFU per ml *E. coli* inoculum by supernatant fractions of *L. reuteri* grown on various indicated substrates at 40 mM concentrations.

Reuterin can be produced in two ways. One procedure is designated as the homologous method and the other as the heterologous method. The homologous method employs *L. reuteri* cells incubated in still culture at 37 degrees C. in a 250 mM glycerol solution. For example, 1 liter of *L. reuteri* cells may be grown for 24–48 hours at 37 degrees C. in Lactobacillus Carrying Medium (LCM). LCM contains (g/L): Trypticase, 10; yeast extract, 5; Tryptose, 3; $KH_2PO_4$, 3; ammonium citrate, 1.5; sodium acetate, 1.0; salts (as in LBS) cystein- HCL, 0.2; and Tween 80, 1 ml. The pH is adjusted to 7.0. Glucose (20 mM final concentration) is added after sterilization. The cells are harvested by centrifugation, suspended in 10 ml of a 250 mM glycerol solution, incubated for 6 hours at 37 degrees C. in still culture, and then removed by centrifugation. Reuterin is present in this supernatant fraction. This procedure and its many obvious variations (e.g., altered cell concentrations and incubation times) provides a simple and effective way to produce reuterin.

The heterologous method involves co-culturing *L. reuteri* together with certain other (heterologous) reuterin-stimulating microorganisms. In this procedure, for example, lower concentrations of *L. reuteri* (e.g., 20–300 ug cell dry weight per ml) are suspended in a glycerol-containing culture medium (as described above) together with cells of a viable heterologous micrororganism (e.g., *E. coli* K12) and incubated as described above. At viable cell ratios (CFU *E. coli* per ml/CFU *L. reuteri* per ml) of 0.5 or higher, reuterin is produced at a stimulated rate (relative to the absence of the heterologous microorganism) and the production rate per *L. reuteri* biomass unit increases in direct proportion to the biomass of the heterologous microroganism. This discovery of the role heterologous microorganisms play in reuterin systhesis was a key to the development of the "feedback regulation" model described below. This "heterologous" cell stimulation appears to require cell to cell contact between viable cells because this stimulation does not occur when the two species are separated from each other by a dialysis membrane in an otherwise identical co-culture system (Table 3). The possibility that the heterologous species is involved at least in part by lowering the redox potential in the *L. reuteri* microenvironment and thereby stimulating reuterin production has not been ruled out as contributory to this stimulatory effect. Reuterin production is not stimulated if the heterologous *E. coli* is not viable (Table 4) or if *L. reuteri* is not viable. Reuterin production by the heterologous method does not depend on the ability of the stimulatory organism to metabolize glycerol. Mutants of *E. coli* unable to metabolize glycerol stimulate reuterin production as effectively as wild-type cells.

Figure 2:
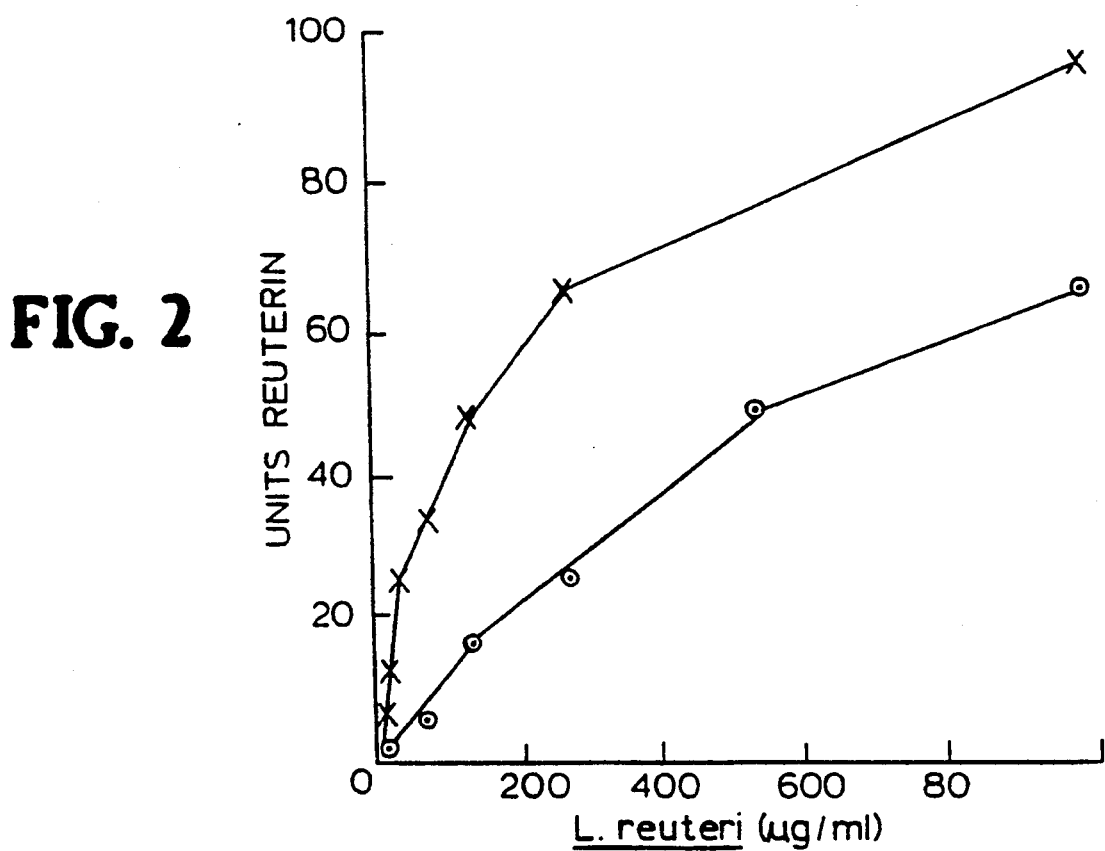
FIG. 2 shows the effect of *L. reuteri* concentration (ug/ml dry weight) on reuterin production after semi-anaerobic incubation of two strains of *L. reuteri* with *E. coli* in a glycerol medium.
Figure 3:
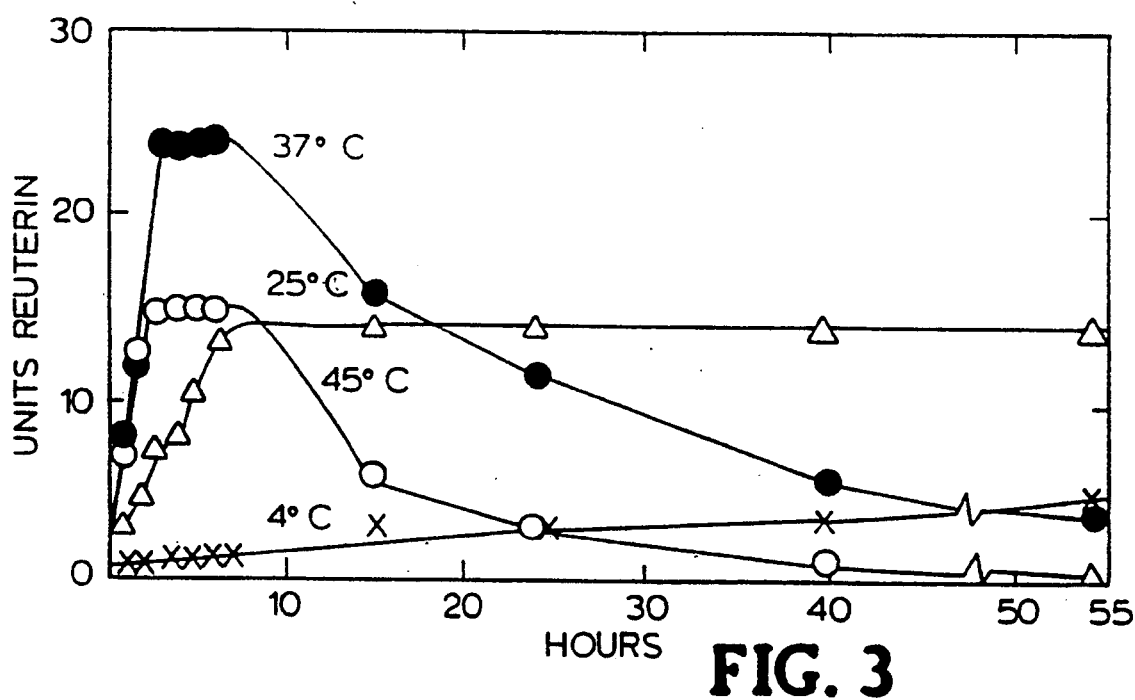
FIG. 3 shows the effect of temperature on reuterin production.
Figure 4:
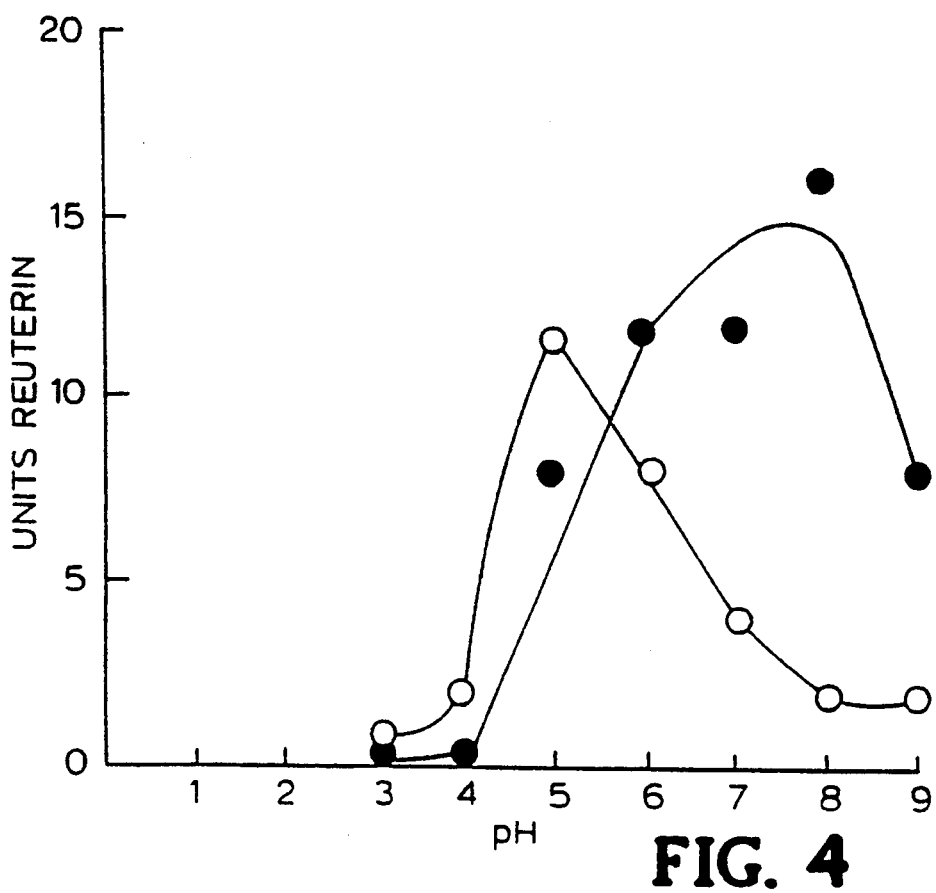
FIG. 4 shows the effect of culture pH on reuterin production.

Reuterin is produced under the physiological conditions that occur in living animals. Reuterin production (using the heterologous method) is initially rapid and proportional to the *L. reuteri* biomass (FIG. 2) but thereafter, production rates per biomass unit decrease presumably owing to a decrease in the viable cell (*E. coli/L. reuteri*) ratio and/or the sensitivity of *L. reuteri* cells to the higher concentration of reuterin produced under these conditions. As also seen in FIG. 2, *L. reuteri* strain 1063 (X) produces greater amounts of reuterin by the heterologous method than does the neotype, strain 20016 (O). Reuterin resistant mutants of *L. reuteri* may produce even higher levels of reuterin. Reuterin production occurs at maximal rates at temperatures between 25 and 37 degrees C. FIG. 3 shows the effect of incubation temperature on reuterin production during semi-anaerobic incubation of *L. reuteri* in a glycerol medium at 4, 25, 37 and 45 degrees C. Reuterin is produced in the pH range 5 to 9 with optimal production at pH 6–8. FIG. 4 shows the effect of culture pH on reuterin production during semi-anaerobic incubation of *L. reuteri* with *E. coli* in a glycerol medium for 3 hours (curve 3) and 24 hours (curve 4). To date all three strains of *L. reuteri* tested produce reuterin: the neotype, DSM 20016, ATCC 27273 (previously classified as *L. fermentum*) and the newly isolated strain 1063. All three strains produce reuterin by the homologous procedure (Table 5). Reuterin production by the heterologous procedure varies among these strains in the following manner: production is greatly, moderately and only slightly stimulated by the heterologous microorganism for strains 1063, 27273 and 20016, respectively.

Example II

Characteristics of the Antibiotic

Reuterin production occurs in the absence of a pH change in the culture medium and in the presence of exogenously added catalase. Its antimicrobial activity is therefore not associated with well-known end products of lactic acid fermentations such as lactic and acetic acids or hydrogen peroxide or with other acidic substances found by others (24, 25). Reuterin remains in the culture fluid after removal of the cells by centrifugation or filtration. Reuterin can be separated from the culture medium and purified by HPLC using water (deionized) or 10 mM $H_2SO_4$ as solvent systems and C-18 solid-phase columns. Reuterin and other products present are detected during HPLC using a refractive index (RI) detector system. An RI peak exhibiting MIC activity elutes in this system between glycerol and 1,3-propanediol. When $14_C$ (uniformly labled) glycerol is used in the reuterin producing system, the reuterin recovered by HPLC is $^{14}$C-labeled showing that this substance is (at least in part) a water soluble derivative of glycerol.

Example III

Antimicrobial Activity

Figure 5:
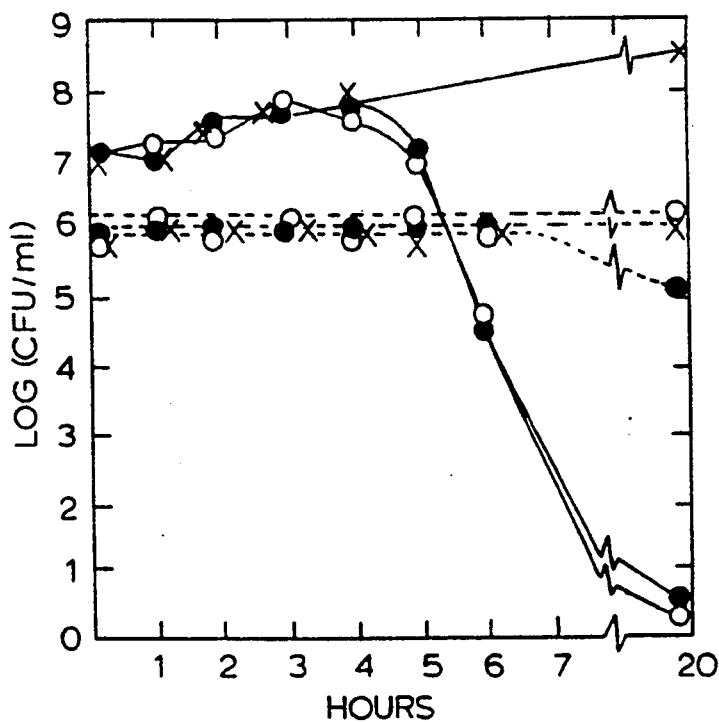
FIG. 5 shows production of reuterin and evidence of bacteriocidal activity.

Reuterin is a broad-spectrum antimicrobial agent. Reuterin functions as a bacteriocide. Production of reuterin and evidence of its powerful bacteriocidal activity are both clearly demonstrated by the data summarized in FIG. 5. The indicated concentrations (CFU per ml) of E. coli (solid lines) and L. reuteri 1063 (dashed lines) were inoculated (zero time) into the glycerol casein hydrolysate medium described above (o), the same medium minus citrate) (•) and the same medium minus glycerol (X). The co-cultures were incubated semi-anaerobically (still cultures) at 37 degrees C. with samples removed at the indicated intervals to determine the numbers (CFU per ml) of E. coli and L. reuteri present. It can be seen from these data that when glycerol was present a substance was produced during the first 3–4 hours which resulted in a 7–8 log decrease in viable E. coli cells during the next few hours. All Gram-negative bacterial genera tested thus far (Escherichia, Shigella, Salmonella, Proteus and Pseudomonas) and all Gram positive genera tested ( Staphylococcus, Streptococcus, Clostridium, Bacillus, Leuconostoc and Lactobacillus) are sensitive to reuterin. Somewhat higher concentration of reuterin are required, however, to kill representatives of the latter three genera. A lower eucaryote, the yeast Saccharomyces cerevisiae, is also killed by reuterin. These discoveries are summarized in Table 6. Also shown in this table is the ability of various species tested to stimulate reuterin production by the heterologous procedure. It is also noted that L. reuteri itself is sensitive to reuterin if exposed to concentrations of 32 MIC units or higher. We also have data showing that reuterin (at a final concentration of approximately 20 MIC units ml$^{-1}$) inhibits in vitro growth of the protozoan parasite that causes Chaga's disease, Trypanosoma cruzi. Whereas control cultures exhibited normal growth and behavior, reuterin treated cells lost motility and ability to divide and exhibited a morphological "rounding-up", indicating loss of viability.

Example IV

Antiviral Activity

Figure 13B:
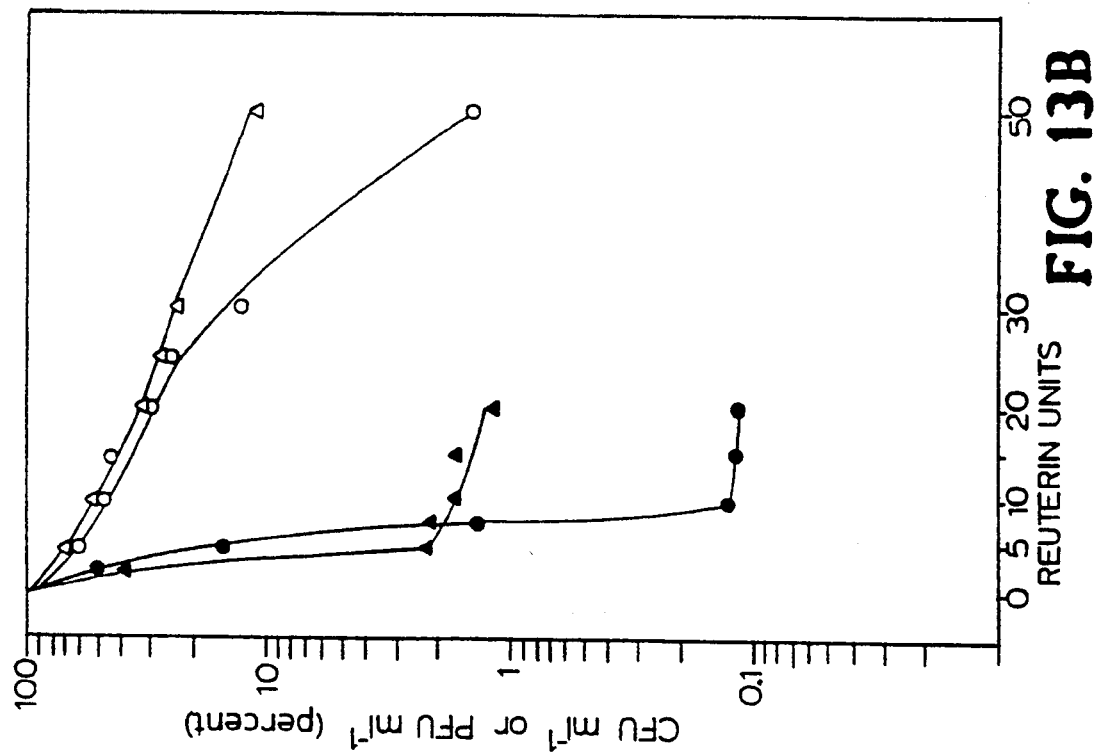
FIG. 13A shows the actual counts of the colony-forming units (CFU's) and plaque-forming units (PFU's) at each reuterin level when reuterin was added to phage-infected bacterial cultures and FIG. 13B shows the percent of CFU's and PFU's.
Figure 13A:
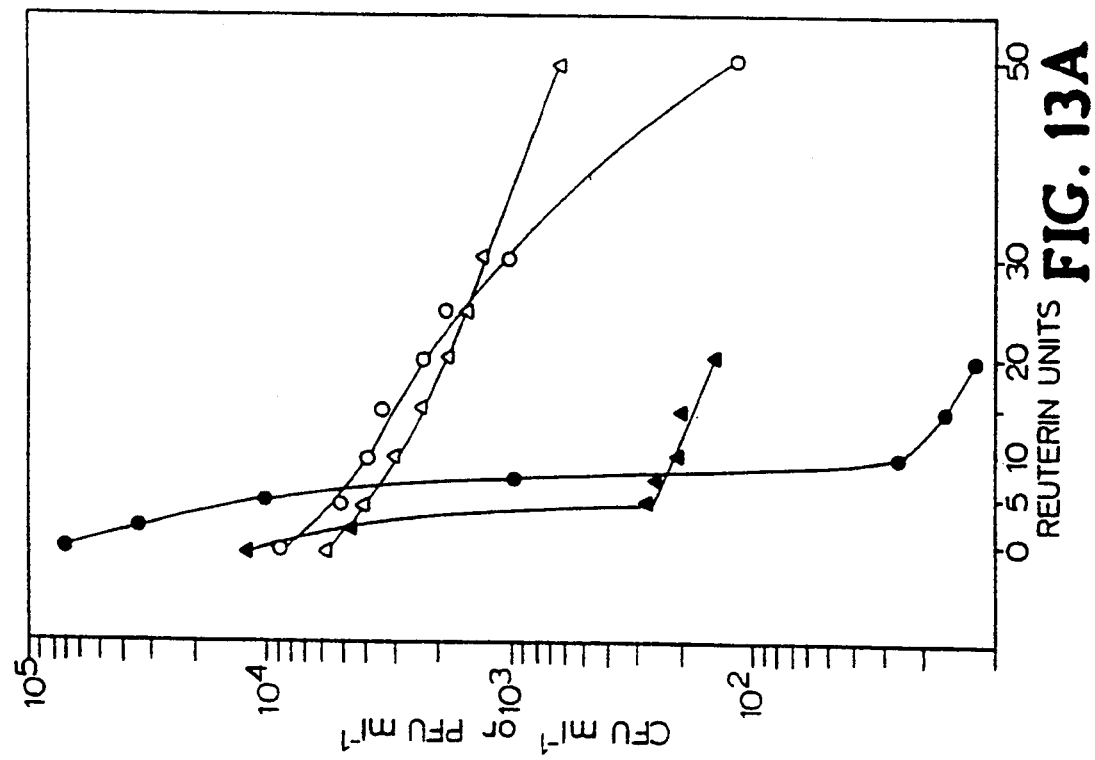

Reuterin is also effective in preventing virus replication. FIG. 13 shows the results of experiments in which 0 to 50 units per ml of reuterin were added to growing bacterial cells of either Escherichia coli or Lactobacillus plantarum infected with bacterial viruses (Lambda phage or phage 8014-B2, respectively). It appears from preliminary results with $^{14}$C-labeled glycerol that 4 ug of reuterin in 0.5 ml solution is about the equivalent of 1 unit of reuterin. After four hours, the number of colony-forming units (CFJs) of the host cell and the number of plaque-forming units (PFUs) of the viruses were assayed using standard microbiological techniques. With no reuterin added, the number of microbial cells had increased about 100-fold in the four-hour period. With E. coli, addition of 10 units of reuterin caused an approximate 100-fold decrease in the number of cells and more than a 1000-fold decrease in the number of PFUs of the lambda phage as compared to the reuterin-free control culture after incubation for four hours. Although the Lactobacillus CFU and PFU decreases due to reuterin were less spectacular and required higher reuterin concentrations than with E. coli, a similar pattern with even greater declines in the PFUs than in the CFUs was observed at reuterin amounts at or greater than 25 units. These results show that reuterin is effective in inhibiting virus production and this effectiveness is above and beyond the effective of reuterin on the bacterial host cells.

Example V

Probiotic Activity

When Lactobacillus reuteri is fed to swine, it is capable of colonizing their gastro-intestinal tract. In preliminary experiments, L. reuteri 1063 cells at concentrations ranging from $10^8$–$10^{10}$ CFU per animal were included in the diets of newborn piglets and viable L. reuteri 1063 cells were recovered from the stools of these animals. These L. reuteri inoculations had no adverse effects on the animals.

Experiments using either adult pigs, piglets (less than 5-days old) or gnotobiotic piglets were performed in which large quantities (about $10^9$ cells) of L. reuteri strain 1063 cells were fed to the animals. After 5–7 days, sufficient L. reuteri cells were still recovered from the animals' feces showing that L. reuteri survived passage through the GI tract and remained long enough in the animal to indicate that colonization has occurred and that reuterin may be produced. Reuterin production by L. reuteri strain 1063 would be expected in the environment of the GI-tract, this tract being the environment from which the L. reuteri strain was originally isolated. Certain media components or other substances such as glycerol that are conducive to reuterin production by L. reuteri may be added to the animal food to optimize the conditions for reuterin production in the GI-tract. Lactobacillus reuteri strains isolated from a variety of species of animals including birds (the term "animals" clearly includes humans and birds), may be fed in quantity to the animal species from which the strains were isolated or to animals of species other than the one from which they were isolated.

Example VI

Inhibition of Ribonucleotide Reductase

Reuterin inhibits ribonucleotide reductase, the first step in deoxyribonucleic acid (DNA) synethesis. In nature there is only one pathway for deoxyribonucleotide synthesis, namely the direct reduction of the corresponding ribonucleotides. Deoxyribonucleotides are highly specialized metabolites and serve only as building blocks for DNA. The enzyme which catalyzes the reduction of ribonucleotides to deoxyribonucleotides is ribonucleotide reductase. This reduction is the first prerequisite step in DNA synthesis and thereby plays an essential role in growth and multiplication of procaryotic and eucaryotic cells and viruses.

The evidence that reuterin inhibits ribonucleotide reductase (EC 1.17.4) activity was obtained using the procedure described by Thelander, Sjoberg and Eriksson in *Methods in Enzymology* (Volume LI), pp. 227–237, 1978. Purified B1 and B2 subunits of the enzyme, encoded by the nrdA and nrdB genes, were used and the spectrophotometric assay was employed as described by the above authors. Briefly, this procedure is as follows: The enzyme was incubated at 25° C. in a reaction mixture containing 200 nmoles ATP, 1.6 umoles $MgCl_2$, 80 nmoles NADPPH, 5 umoles N-2-hydroxyethyl-piperazine-N'2-esthanesulfonic acid buffer (pH 7.6), 300 pmoles thioredoxin, 40 pmoles thioredoxin reductase, 10 nmoles EDTA, and 65 nmoles dithiothreitol in a final volume of 0.13 ml. The reaction was started by the addition of 75 nmoles CDP, and the oxidation of NADPH was monitored at 340 nm with a Zeiss automatic recording spectrophotometer equipped with microcuvettes. Before addition of CDP, the background oxidation of NADPH was recorded and this background was subtracted from the NADPH oxidation observed after addition of CDP.

The reuterin used in these tests was prepared by the homologous method and contained 256 MIC units of activity per ml. Undiluted and various dilutions of reuterin were added (in 1 ul amounts) to the reaction mixture to determine the effect of this substance on ribonucleotide reductase activity. The results of this experiment are summarized in Table 7. They show that reuterin is an effective inhibitor of the B1 subunit of this enzyme. It was also noted that thioredoxin (required for enzyme activity) was also sensitive to reuterin.

The ability of reuterin to inhibit growth of bacteria, yeasts, molds, porotozoa, viruses and neoplastic and normal animal cells can thus at least in part be attributed to its ability to inhibit DNA synthesis by inhibiting de novo production of deoxyribonucleotides.

Example VII

Reuterin is an effective food preservative

Ground beef purchased from a local supermarket was divided into 4 portions. One portion was untreated, the others were treated with 10, 50 and 100 units of reuterin per gram of the meat. All meat samples were stored at 4 degrees C. with samples taken at indicated days for bacteriological analysis.

Figure 14:
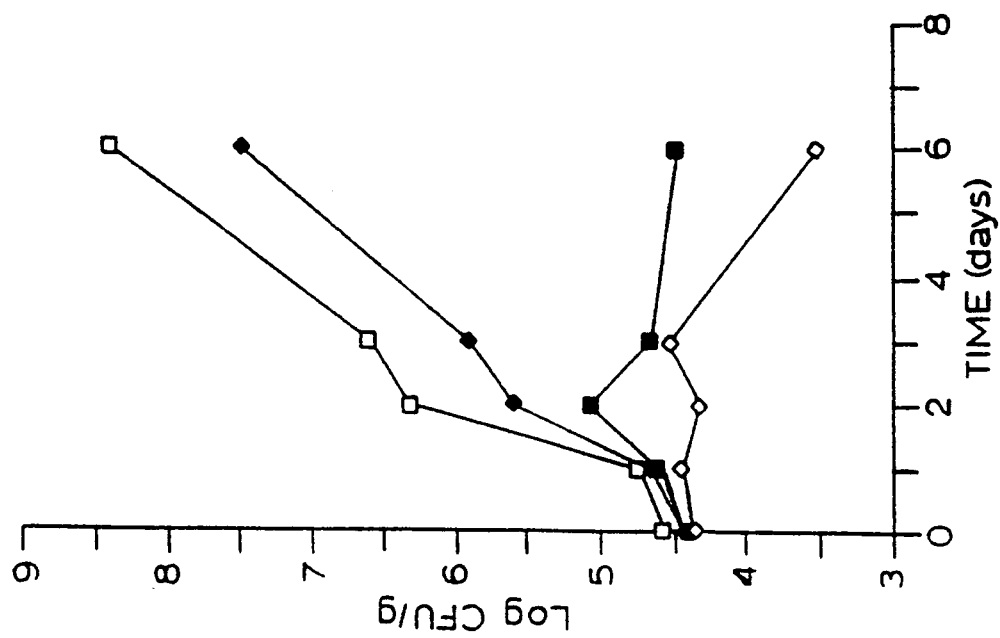
FIG. 14 shows the effect of reuterin on ground beef microflora.

Beef samples were removed and diluted 1:10 (1 g beef: 9 ml sterile $H_2O$). Subsequent decimal dilutions were made as needed and samples were plated onto Difco Nutrient Agar. These samples were incubated at 27° C. for 24 hours and counted as colony forming units per gram ground beef (CFU/g). The data show that reuterin significantly reduced the CFU/g (FIG. 14) (□, control; ◆, 10 units reuterin; ◆ 50 units reuterin; and , 100 units reuterin). With the higher levels of reuterin (50 and 100 units per g) the indigenous population of bacteria was reduced and remained greater than 4 log units lower than the control sample through the 6-day test period.

Figure 15:
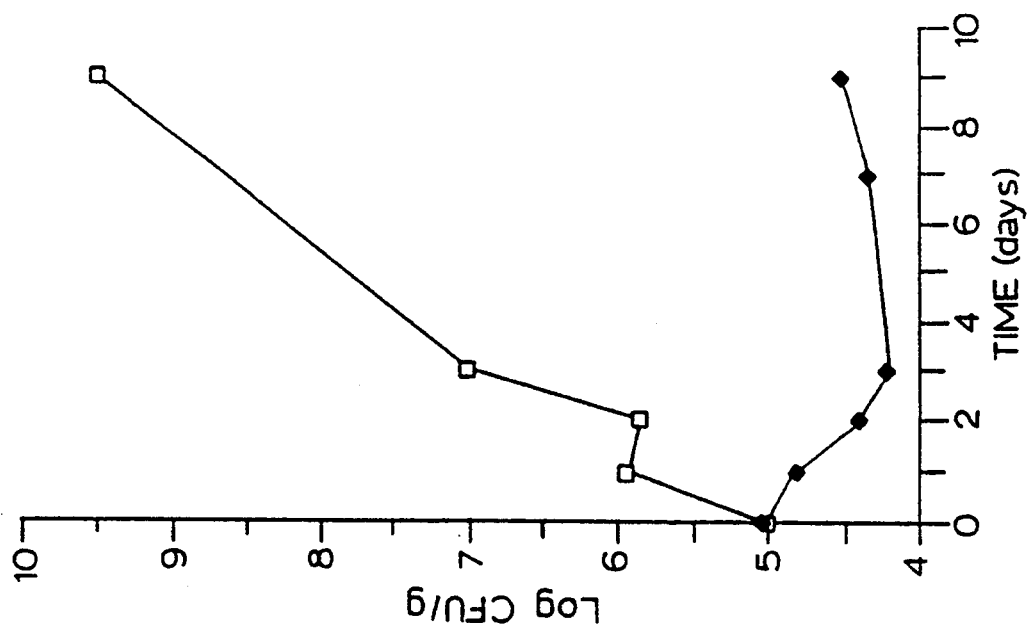
FIG. 15 shows the effect on reuterin on E. coli-inoculated ground beef microflora.

Ground beef purchased from a local supermarket was thoroughly inoculated and mixed with approximately $10^5$ CFU/ml of *E. coli* K12 cells. After mixing, the material was divided into 2 portions. One portion as an untreated control (no reuterin), the other portion received 75 units (U) of reuterin per gram of beef. Samples were stored at 4° C. with portions removed at indicated times for bacteriological analysis. In this experiment the determination of viable cells (CFU/g beef) was conducted as described for FIG. 14 except that Difco McConkey's Agar (relatively specific for coliform-like bacteria) was used. It can be seen in FIG. 15 (□, control; ◆, 75 units reuterin) that reuterin reduced the initial population of bacteria and kept these numbers low throughout the 9-day incubation period.

Example VIII

*Lactobacillus reuteri* plus glycerol constitutes a novel effective food preservation process. Evidence for this was obtained using storage of fish as a model system. This study was conducted as follows: Fish fillets (Herring, *Clupea harengas*) were dipped in the following treatment solution:
control: no treatment
glycerol: 250 mM glycerol solution
strain 1068: 250 mM glycerol solution containing $4 \times 10^9$ CFU per ml *L. reuteri* 1068 (a non-reuterin producing strain)
strain 1063: 250 mM glycerol solution containing $4 \times 10^9$ CFU per ml *L. reuteri* 1063

The fillets (2 parallel samples each) were kept in large Petri dishes at 8° C. for 4 days in a refrigerator. The ammonia content and CFU of relevant bacteria (i.e., spoilage psuedomonads and added lactobacilli) were then analyzed to evaluate the shelf-life of the food product. The results summarized in Table 8 indicate:

(i) the added lactobacilli (counted as total lactobacilli using glucose Lactobacillus Selection Medium, described earlier) and the *L. reuteri* CFU (counted as total heterofermentative lactobacilli detected using L-arabinose Lactobacillus Selection Medium) survive well at 8° C. but do not multiply to any significant extent.

(ii) *L. reuteri* 1063 significantly retarded growth of the spoilage psuedomonads. *L. reuteri* 1068 did so to some extent but not enough to prevent spoilage which is generally indicated by a log 8.4 pseudomonad count.

(iii) the retarding effect of *L. reuteri* and glycerol on spoilage bacteria has a strong reducing effect on ammonia liberation.

(iv) a food preservative effect of *L. reuteri* plus glycerol is indicated for all kinds of food spoilage.

Example IX

Reuterin Is a Product of Glycerol Fermentation

Reuterin is a new product associated with the same type of heterolactic fermentation of glycerol that occurs in other Lactobacillus species. Reuterin can be isolated and identified as a product of glycerol fermentation by *L. reuteri* using HPLC. Glycerol, 1,3-propanediol and β-hydroxypropionic acid (all pure commercial preparations) were shown to be essentially devoid of antimicrobial activity when tested in concentrations as high as 0.125M.

The production by *L. reuteri* of reuterin plus 1,3-propanediol and β-hydroxypropionic acid during the fermentation of glycerol was established using HPLC analysis. Representative data are shown in FIG. 6. To prepare the sample, one liter *L. reuteri* culture (grown in LCM containing 20 mM glucose at 37 degrees C. for 48 hours) is harvested by centrifugation, washed twice with sterile sodium phosphate buffer (pH 7.5) and suspended in 10 ml of 0.25M sterile glycerol. After 6 hours incubation at 37 degrees C., the cells are removed by centrifugation and the supernatant fluid (hereafter referred to as the sample) is analyzed for reuterin by the MIC test described earlier and by HPLC as described below. In some experiments 5 uCuries of $^{14}C(U)$ glycerol were included with the 0.25M glycerol. Samples were passed through a 0.2 to 0.45 micron bacteriological filter and stored aseptically at 2 degrees C. prior to injection into the HPLC apparatus.

The HPLC analysis was performed as follows: a 20–100 ul fraction of each sample was injected into a Beckman HPLC apparatus fitted with a single or two tandem C-18 analytical columns. The samples were eluted with distilled-deionized water passed through a 0.2 to 0.45 micron filter. Elution rates were 1.0 to 1.5 ml per min and the samples were monitored using a Waters 410 differential refractometer. Refractive index (RI) changes were automatically recorded and plotted as RI (ordinate) vs. elution volume/time (abscissa) proceeding from right to left on the graphs shown. The total elution time for each sample was approximately 15 minutes, with peaks 1, 2 and 3 eluting at approximately 8, 7 and 6 minutes respectively.

HPLC analyses of samples prepared as described above and eluted with water are shown in FIGS. 6A–6E. Included here are samples prepared using *L. reuteri* 1063 at 128 and 512 MIC units (graphs 6A and 6B respectively, *L. reuteri* 20016 (graph 6C) and *L. reuteri* ATCC 27273 (graphs 6D and 6E). Only substances designated as peaks 1, 2 and 3 were identified in these elutions. Peaks 1 and 3 were identified as 1,3-propanediol and glycerol by use of reference standards and by IR spectral identification of the isolated peaks respectively. Under these conditions, Peak 2 always elutes as the characteristic broad peak seen in these graphs, and it is the only substance eluting from the samples which has biological activity as determined using the MIC assay. It is thus identified as the antimicrobial substance termed reuterin. Three further analyses support the conclusion that peak 2 is reuterin. First, the amount of material present in peak 2 increases in direct proportion to the MIC value of the original sample. This is seen in graphs 6A and 6B representing reuterin produced by *L. reuteri* 1063 in samples having MIC titers of 128 and 512 respectively. Second, all *L. reuteri* strains tested thus far produce reuterin determined by MIC assay and in each case peak 2 is present (see graphs 6A–6E). All other Lactobacillus species tested to date lack comparable biological activity (MIC assay) and when analysed by HPLC exhibit little or no material eluting in the peak 2 region. Third, a spontaneous variant or mutant of *L. reuteri* ATCC 27273 has been isolated and purified. This variant produces considerably lower levels of reuterin (as determined by the MIC assay), shows weak to no inhibitory zones in the glycerol-*E. coli* overlay plate assay and as seen in graph 6E produces much less of the substance eluting in the peak 2 region as compared to its parental (wild-type) strain (graph 6D).

Figure 6F:
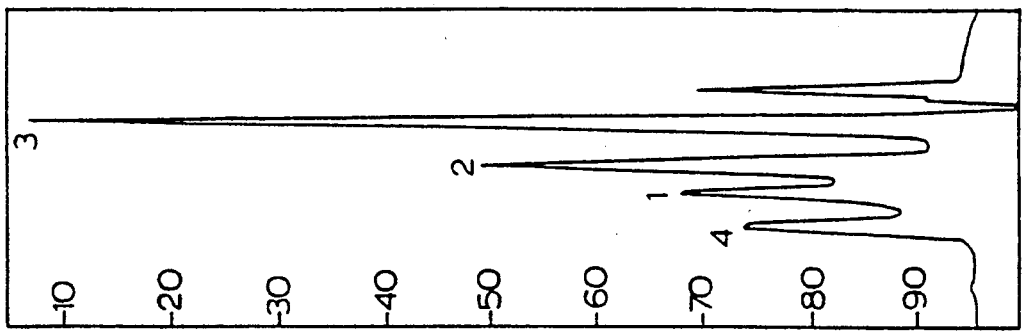
FIG. 6 show the results of High Performance Liquid Chromatography (HPLC) analyses of *L. reuteri* samples.
Figure 6D:
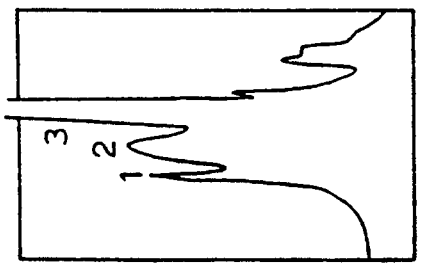
Figure 6E:
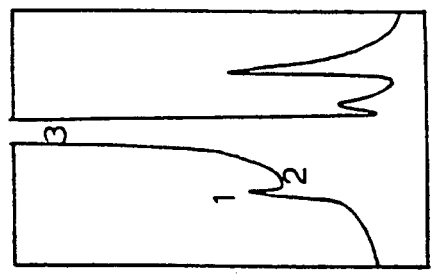
Figure 6C:
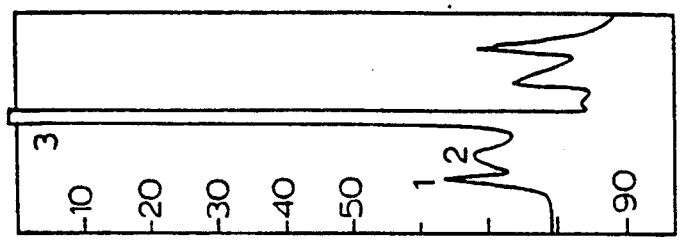
Figure 6B:
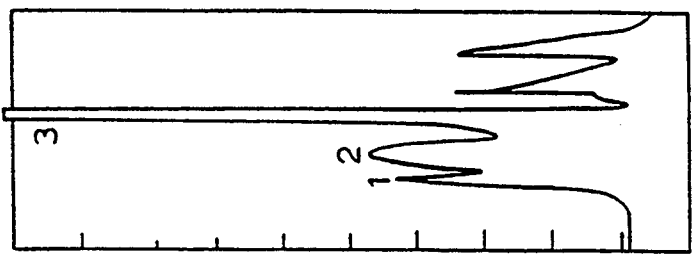
Figure 6A:
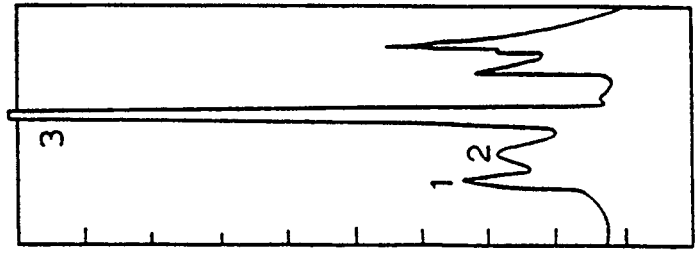

When 0.01M $H_2SO_4$ was used as the elution solvent, a $\beta$-hydroxypropionic acid peak was resolved as seen in FIG. 6F. The sample used in this experiment was obtained from strain 1063 and had 1024 MIC units of reuterin. When $^{14}C(U)$-glycerol was included in an essentially identical experiment separated by HPLC using 0.01M $H_2SO_4$ as solvent and collected as separate peaks for radioactivity determines (Packard Liquid Scintillation Spectrometer) the following results were obtained: 2,777; 40,776; 53,228 and 61,428 total cpm were recovered as $\beta$-hydroxypropionic acid (peak 4), 1,3-propanediol (peak 1), reuterin (peak 2) and unused glycerol (peak 3), respectively. These results and analytical data on reuterin presented below indicate that glycerol is fermented under these conditions according to the following reaction:

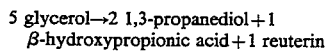

Example X
Preliminary Reuterin Characterization

Figure 7:
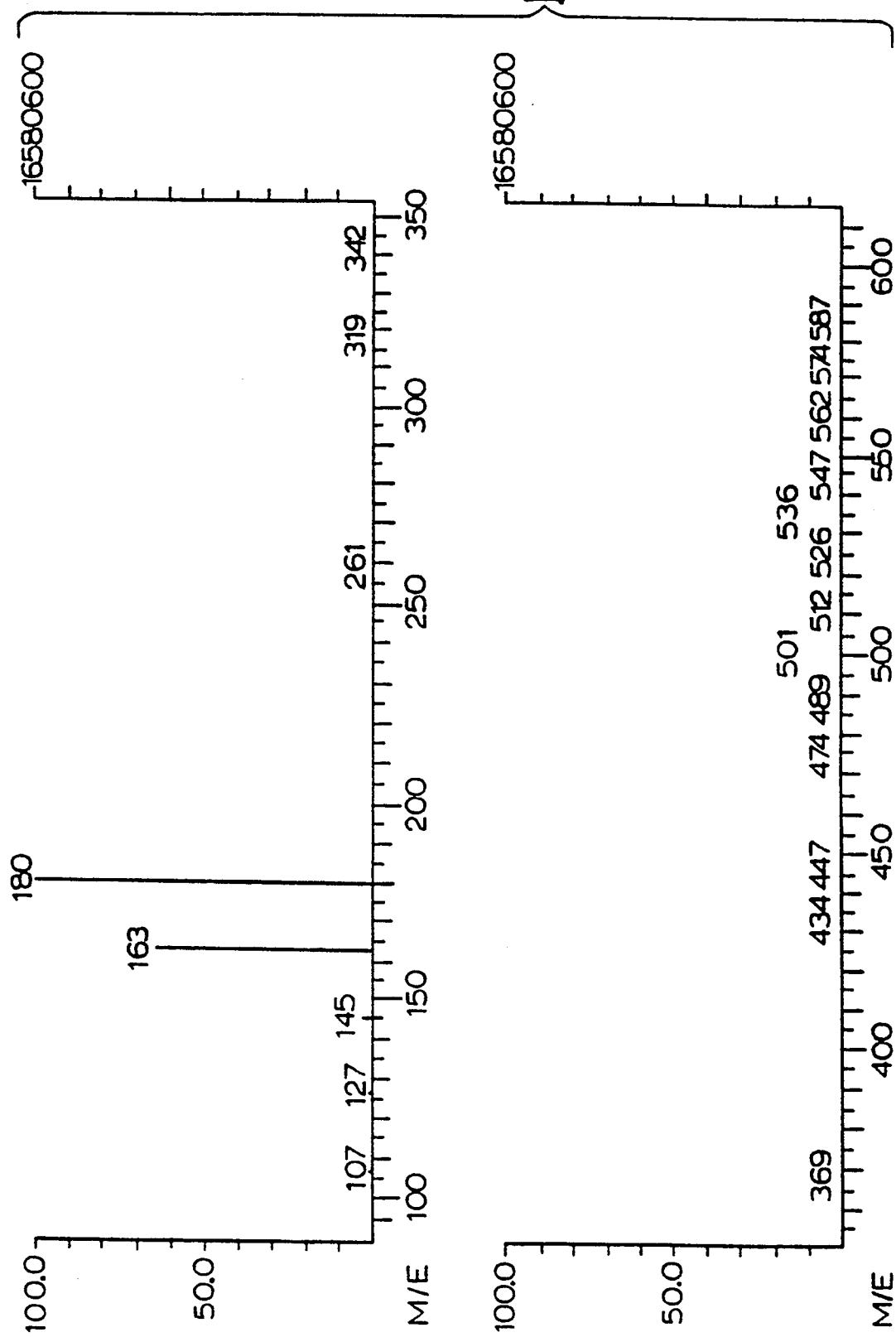
FIG. 7 shows the positive ion mass spectrum of reuterin.
Figure 8:
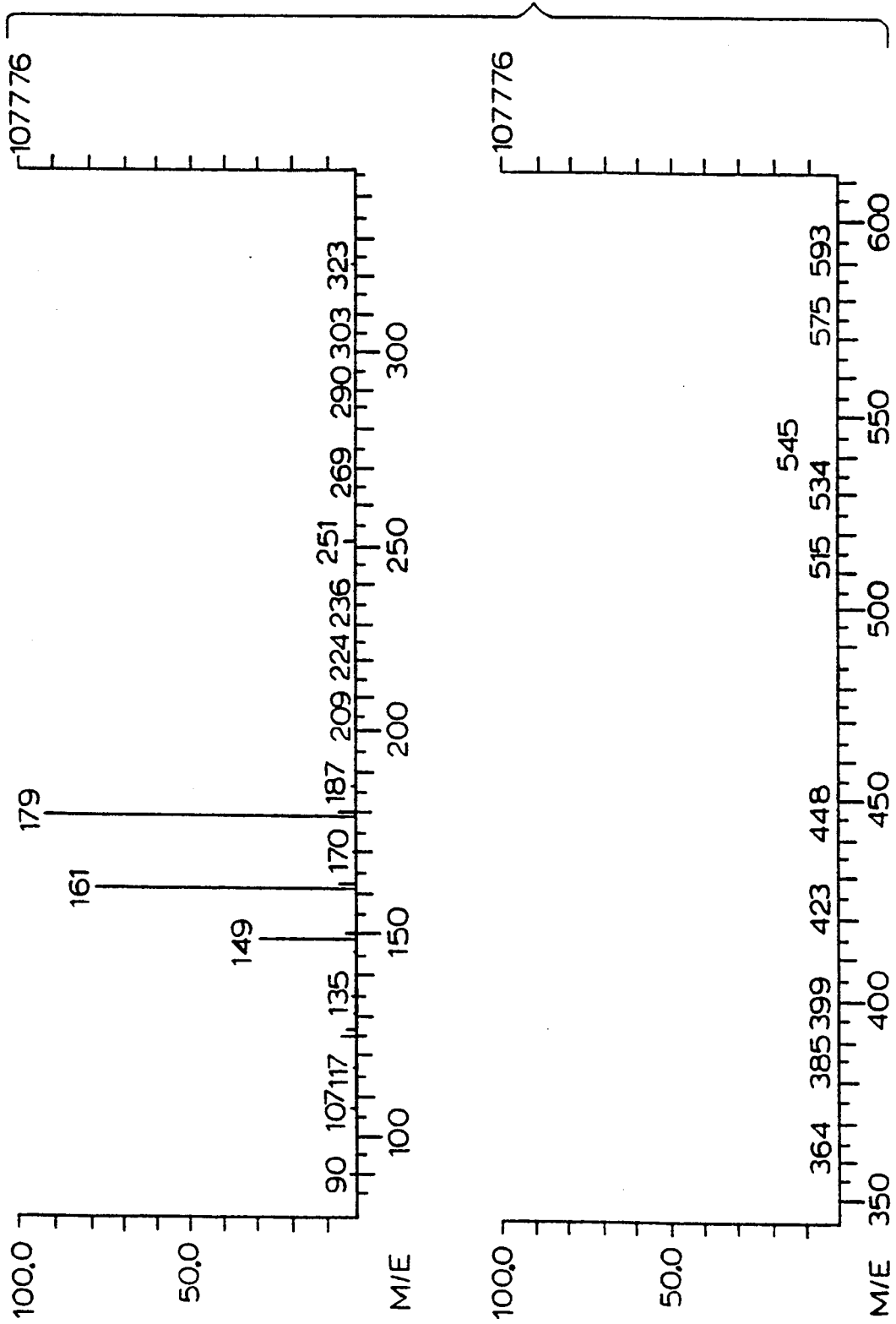
FIG. 8 shows the negative ion mass spectrum of reuterin.

Characterizations of reuterin crude preparations indicated that it is highly soluble in water, resistant to nucleases and proteases and liable to heat (100 degrees C. for 10 minutes) particularly at pH values of 9.0 or higher. Reuterin is clearly not a bacteriocin. Preliminary analytical analyses have been conducted on essentially pure reuterin (with some glycerol present) isolated by HPLC as described above. Samples were submitted to the Research Triangle Institute (Research Triangle Park, N.C.) and the Department of Chemistry (N.C. State University, Raleigh, N.C.) for mass, nuclear magnetic resonance and infrared spectral analyses. These data are summarized in FIGS. 7–11. The LCMS analyses were performed on a Finnigan 4500 HPLC/MS system using a Vestec Interface. Separation was effected using the Aminex 87H column as with an eluent flow rate of 0.8 ml/mn. Both the positive ion (FIG. 7) and the negative ion (FIG. 8) mass spectra (relative intensity plotted on the ordinate axis, mass to energy charge, m/e value, on the abscissa axis) indicated a molecular weight of approximately 162 grams per mole. This preliminary information together with (i) the radioisotope analyses described above and (ii) the observation that reuterin gives a positive Schiff's reaction (indicating presence of an aldehyde functional group) indicated that reuterin has a molecular formula of $C_6H_{10}O_5$ and the following structure:

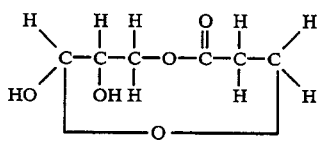

Figure 9:
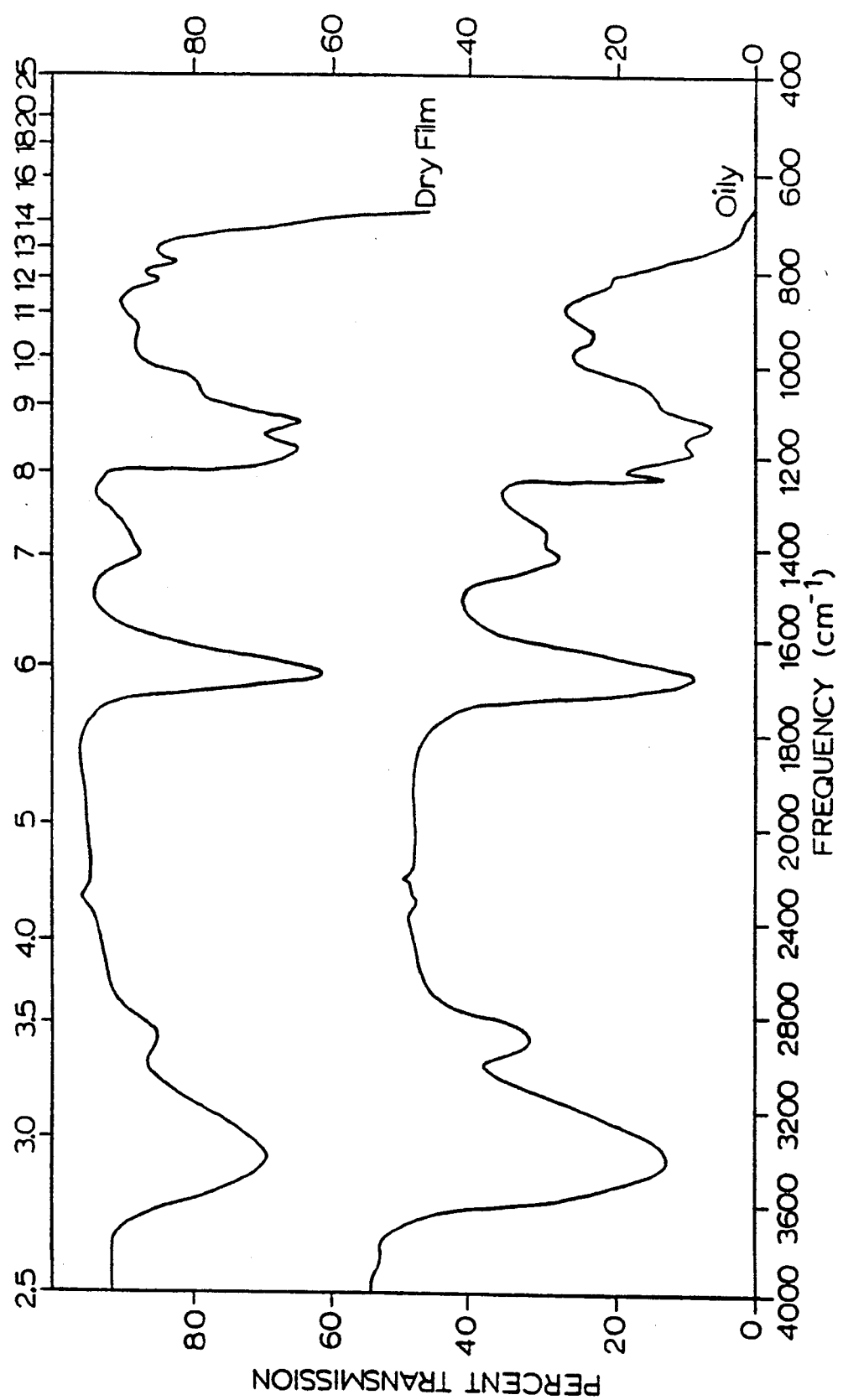
FIG. 9 shows the infrared spectrum of reuterin.
Figure 10:
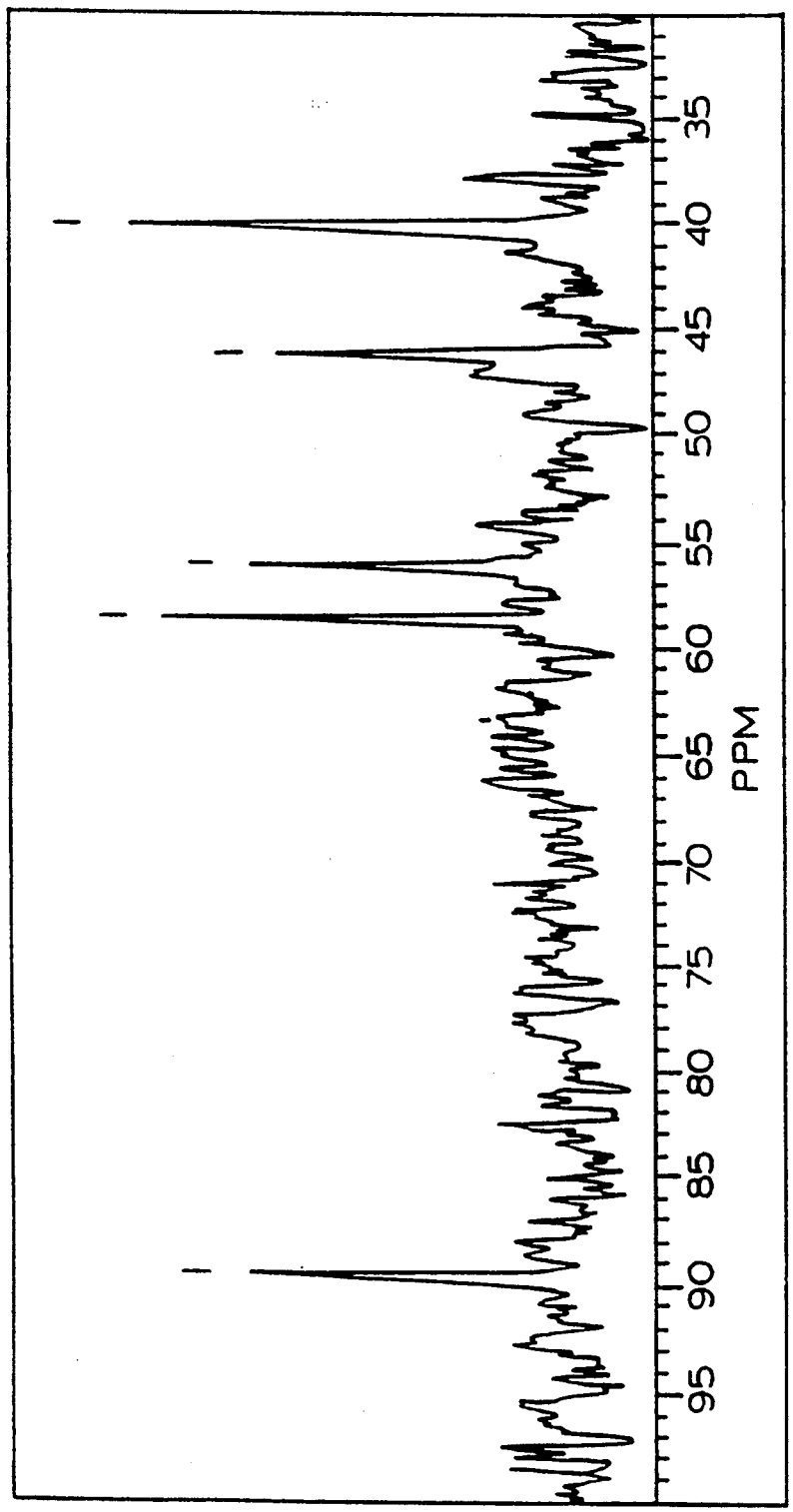
FIG. 10 shows the carbon NMR spectrum of reuterin.
Figure 11:
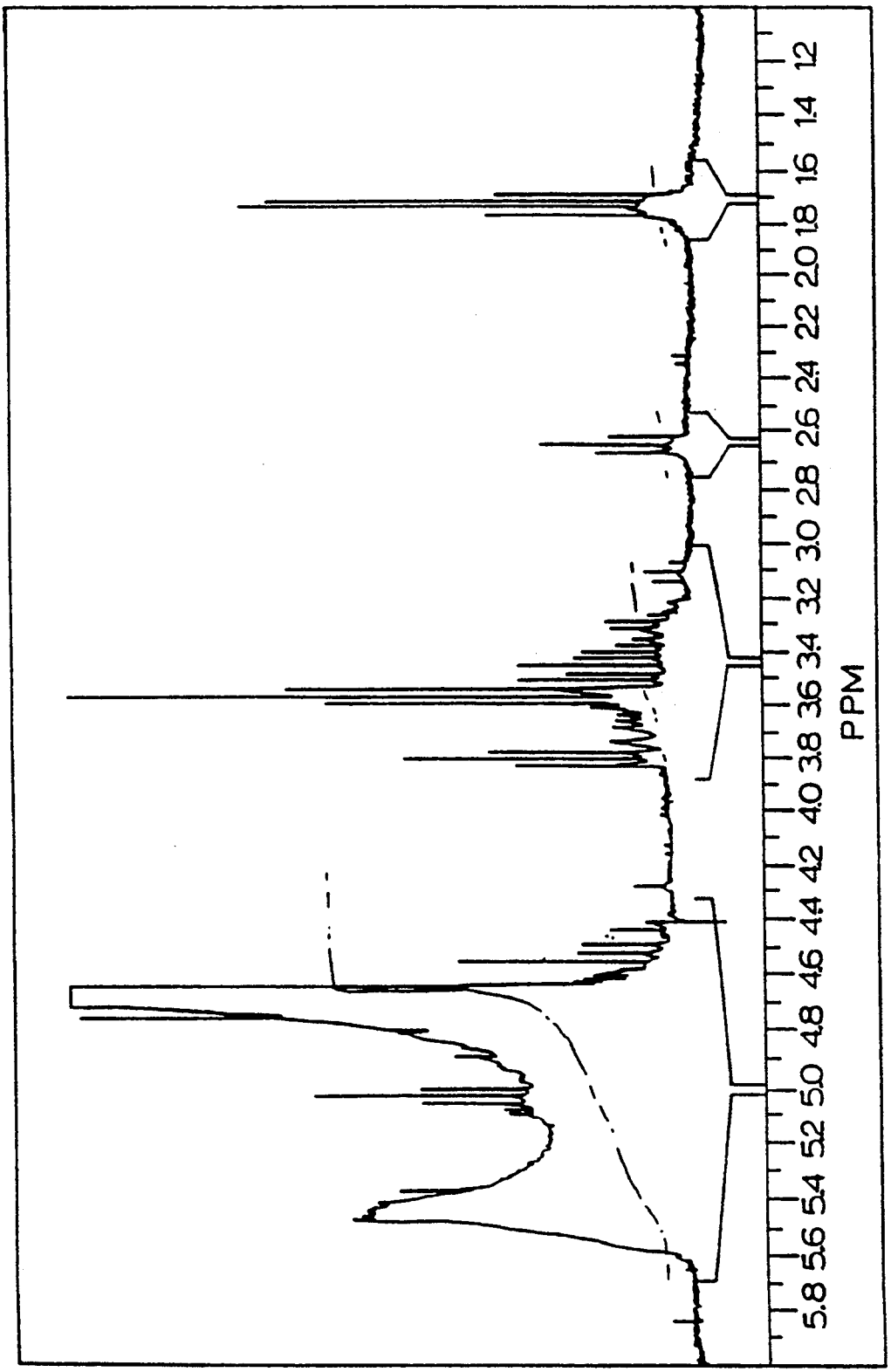
FIG. 11 shows the proton NMR spectrum of reuterin.

The infrared spectral analysis shown in FIG. 9, the carbon nuclear magnetic resonance (NMR) spectral analysis shown in FIG. 10 and the 250 mega Hertz proton NMR analysis shown in FIG. 11 are consistent with this proposed structure for reuterin. These NMR spectral data are computerized plots of radiation absorption (ordinate axis) verus magnetic field sweep (abscissa axis). Information on the exact structure was obtained when large quantities of absolutely pure reuterin became available.

Based on the carbonhydrate-like structure for reuterin postulated from the preliminary data, including an aldehyde carbon on one end of the molecule and an alcohol carbon at the other end, the existence of this substance as a hemiacetal corresponding to reaction between the aldehyde group and the terminal hydroxyl group was indicated. A three dimensional molecular model of such a structure revealed a molecule bearing close resemblance to a pentose such as D-ribose.

On this basis it was postulated that reuterin could be a D-ribose analogue able to compete with ribonucleotides for their ribose-recognition site(s) on the first enzyme specifically involved in DNA synthesis, ribonucleotide reductase. Reuterin thus could inhibit the first step specific for DNA synthesis by inhibiting the conversion of ribonucleotides to deoxyribonucleotides. If reuterin were a pentose analogue and bound at the reductase site, it would be expected to bind preferentially in fast-growing malignant cells such as cancer cells. These propositions are consistent with (i) the proposed structure of reuterin, (ii) the speed with which reuterin exerts its bacteriocidal effect (experimental data demonstrate inhibition of *E. coli* growth shortly after addition of reuterin) and (iii) the fact that both procaryotes and eucaryotes (*S. cerevisiae* and *Trypanosoma cruzi*) are sensitive to reuterin. Thus, reuterin could be considered to be an anti-fungal, anti-parasite, anti-viral and anti-cancer agent as well as an antibacterial agent.

Example XI
Production of purified reuterin for chemical analysis

A 1% inoculum of overnight culture of *Lactobacillus reuteri* 1063 (1) was grown in modified Lactobacillus Carrying Medium with glucose (LCMG) for 24 hours. Modified LCMG consists of the following per liter of solution: 5 g yeast extract, 10 g trypticase, 3 g tryptose, 3 g potassium phosphate (monobasic), 3 g potassium phosphate (dibasic), 2 g ammonium citrate, 1.15 g sodium acetate.$3H_2O$, 5 mg magnesium sulfate.$7H_2O$, and 0.31 mg manganous sulfate, 0.2 mg ferrous sulfate.$7H_2O$, and 0.5 mg L-ascorbic acid. This medium was then autoclaved and 10 ml of filter sterilized 2M glucose were added to the cooled medium. Cells of *L. reuteri* were harvested by centrifugation at 4000×g for 10 minutes and washed twice with 50 mM sodium phosphate buffer (pH 7.5).

After washing, *L. reuteri* was suspended to a concentration of 10 mg cells/ml deionized water. Sterile glycerol was added until a concentration of 250 mM was achieved. This cell suspension was then incubated at 37 degrees C. for 3 hours in order to produce and accumulate reuterin. Cells were then pelleted at 4000×g for 10 min and discarded. The supernatant fluid was filtered through a 0.45 micron filter (Acrodisc) to remove remaining cells and subsequently used for isolation of reuterin.

The purification of reuterin was accomplished using a 1×30 cm glass column packed with AG 50 W, 8% crosslinked, −400 mesh resin from Biorad (Richmond, Calif.). A solvent composed of 60% acetonitrile/40% distilled deionized water containing 1.1 g trifluoroacetic acid per liter was delivered via a Beckman 110A HPLC pump. The solvent flow rate was 1.5 ml/min and detection was accomplished with a Waters 410 differential refractometer using a sensitivity of 2× and a scale factor of 5. 400 ul of supernatant fluid was injected using an Altex 210 injector (Beckman) with a 500 ul sample loop and fractions were collected manually. Fractions were then rotavaporated under aspiration at ambient temperature to remove acetonitrile. Samples were subsequently lyophilized to dryness using a Virtis 10-030 lyophilizer. Purity was assessed by passing portions of the fractions through an Aminex 87H analytical column (Biorad).

The first of two fractions eluted from the column at 15 and 19 min and reuterin was found to be present in the first peak. The second fraction had an elution time of approximately 19 min. The front portion of the reuterin containing fraction contained a heavy shoulder which was assumed to be betahydroxypropionic acid and was therefore not collected. The middle portion of the reuterin peak was collected and dried by rotavaporation followed by lyophilization. This process produced a water white, viscous liquid which when rechromatographed under analytical conditions using an Aminex 87H column, produced a single peak which coeluted with the activity peak. The collected fraction also contained bacteriocidial activity as determined by MIC assay. No other collected fractions showed bacteriocidal activity. The purified fraction was also subjected to analysis for the presence of proteins using the Bio-Rad protein assay (Bio-Rad, Richmond, Calif.). The presence of protein could not be detected.

Example XII

Fourier Transform Infrared Analysis of Purified Reuterin

Reuterin was subjected to Fourier Transform Infrared Analysis (FTIR) to determine the chemical groups present within the molecule. The samples were analyzed on a Perkin Elmer 1550 FTIR with a Perkin Elmer 7500 Data Station. The results obtained are shown in FIG. 16. It can be seen that the molecule contained hydroxyl functionality as inferred by the presence of a large C—O stretch band at 1050-1150 $cm^{-1}$ and a broad O—H stretch band at 3450 $cm^{-1}$. A C=D stretch indicative of aldehydes was observed at 1730 $cm^{-1}$. Typical alkane C-H stretches were present at 2880 and 1380 $cm^{-1}$.

Example XIII

Liquid Chromatography/Mass Spectrometry

Analysis of purified reuterin LC separation was accomplished on an Aminex 87H analytical column (Biorad, Richmond, Calif.) with a flow rate of 0.8 ml/min of 65% distilled deionized water and 35% acetonitrile containing 1.0 gm of concentrated sulfuric acid per liter. The solvent stream was mixed with 0.3M ammonium acetate post column and introduced via a Vestec interface (Vestec, Houston, Tex.) into a Finnigan 4500 HPLC/MS system (Finnegan, San Jose, Calif.). Positive ion detection was employed with a vaporizer temperature of 210° C. and a source temperature of 250° C. The electron energy of the source was 1000 eV.

LC/MS analyses were carried out on reuterin with post column addition of ammonium acetate. The base peak occurred at 166 M/E units as is indicated by the data shown in FIG. 17. This ion was interpreted to be the ammonium adduct of the molecular ion. This would indicate a molecular weight of 148 which corresponds to the molecular weight of reuterin. The signal at 148 was predicted to be a loss of water from the adduct ion and the signal at 130 represented the adduct ion with the loss of two molecules of water. The signal present at 101 was believed to be from the background solvent effects.

Example XIV

Nuclear magnetic resonance spectroscopy of purified reuterin

Proton and carbon NMR studies were carried out in both deuterium oxide and deuterated methanol from Aldrich (Milwaukee, Wis.). Proton NMR was run on a Bruker WM 250 FTNMR (Bruker) operated at 250 MHz. Carbon 13 spectra were generated on an IBM NR-100 AF FTNMR (IBM Instruments, San Jose, Calif.) operated at 25 MHz with a superconducting magnet. Data processing was accomplished on an Aspect 3000. In the NMR studies in deuterium oxide, Carbon 13 NMR spectra possessed six signals at chemical shifts of 40.1, 46.3, 56.2, 58.7, 89.7, and 207.7 ppm. The signal at 207.7 ppm was interpreted as an aldehydic carbon, those at 89, 58, and 56 ppm as oxygen linked, and those at 46 and 40 ppm as aliphatic moieties.

Figure 19:
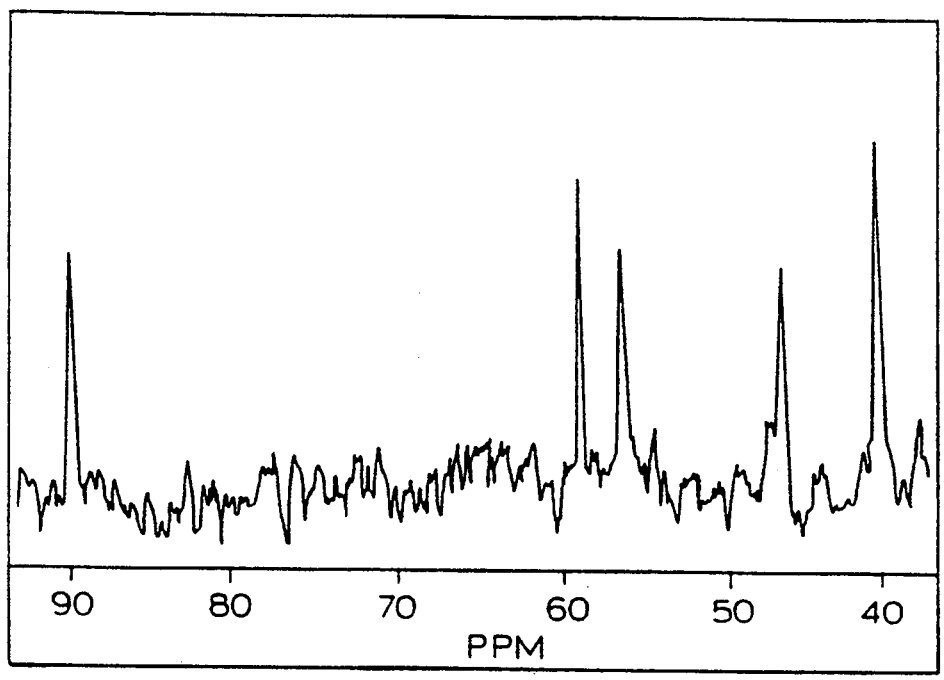
FIG. 19 shows the proton spectrum of reuterin in deuterium oxide.
Figure 18:
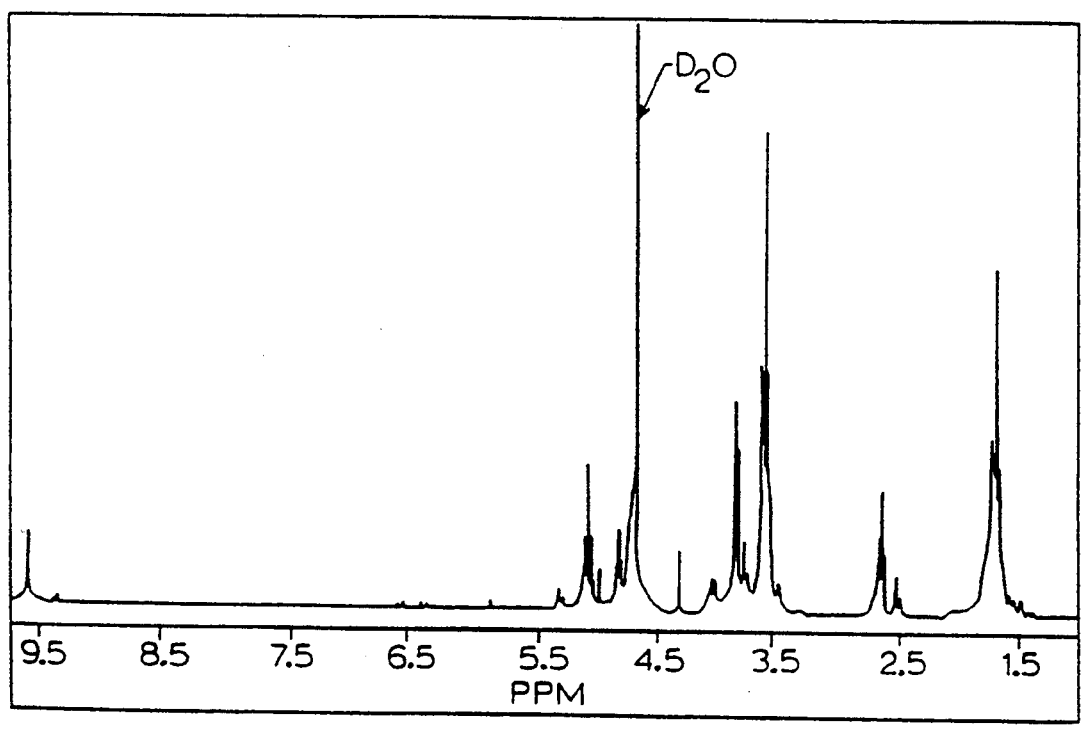
FIG. 18 shows the carbon-13 spectrum of reuterin in deuterium oxide.

The carbon and proton spectra are presented in FIGS. 18 and 19. Decoupling as well as signal splitting patterns led to the initial proposal of the structure shown in FIG. 20. The proton signal at 9.5 ppm (carbon 1) was found to be affected when the signal at 2.6 ppm (carbon 2) was saturated. Protons associated with carbon 2 split into what appeared to be a triplet but upon close examination was actually seen as a sextet (triplet split by non-equivalent proton on carbon 1). The coupling pattern of protons on carbon 2 was found to be altered by saturation of signals at 9.5 and 3.7 ppm (carbons 1 and 3) and therefore was predicted to exist adjacent to both carbons 1 and 3. The splitting pattern of the signal at 3.7 ppm (carbon 3) is a triplet and was affected by saturation of the signal at 2.6 ppm. These patterns fit the predicted structure proposed for carbons 1, 2, and 3 as CHO—CH2—CH2—O—R.

The proton signal at 5.0 ppm (carbon 4) appeared as a triplet and was affected only by saturation of the signal at 1.6 ppm. Saturation of signals at 5.0 and 3.5 ppm led to alterations in the splitting pattens at 1.6 ppm (carbon 5). The protons on carbon 5 possess a complicated splitting pattern which was assessed as a quartet. Protons giving rise to the triplet at 3.5 ppm (carbon 6) were affected only by saturation of the signal at 1.6 ppm (carbon 5). Signal patterns and chemical shift data for this half of reuterin led to prediction of the structure R—O—CHOH—CH2—CH2OH associated with carbons 4, 5 and 6. The hemi-acetal oxygen present in the middle of the molecule (FIG. 20) would prevent coupling of the two halves as was observed. Proton chemical shifts of the predicted structure fit those for known values.

The breadth of the signals at 1.7, 3.6, and 5.0 ppm prevented calculation of the area under each peak used for determining the number of protons giving rise to each signal. Such breadth may be the result of related or transient forms of the molecule existing in equilibrium when water is used as the solvent.

The signal pattern of reuterin in deuterated methanol was distinctly different from that observed in deuterium oxide. The carbon-13 pattern contained only 3 sets of signals at 36.8, 58.9, and 103.9 ppm. Carbon-13 signals around 104 ppm had been observed in disaccharides such as lactose for the carbon shown below:

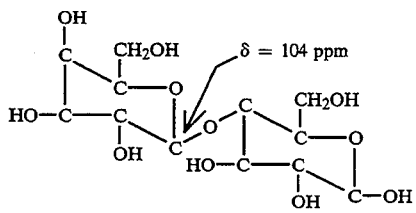

Figure 22:
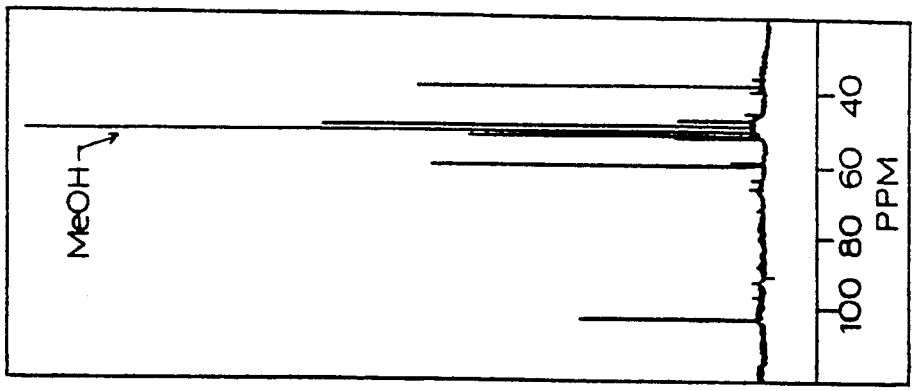
FIG. 22 shows the proton spectrum of reuterin in deuterated methanol.
Figure 21:
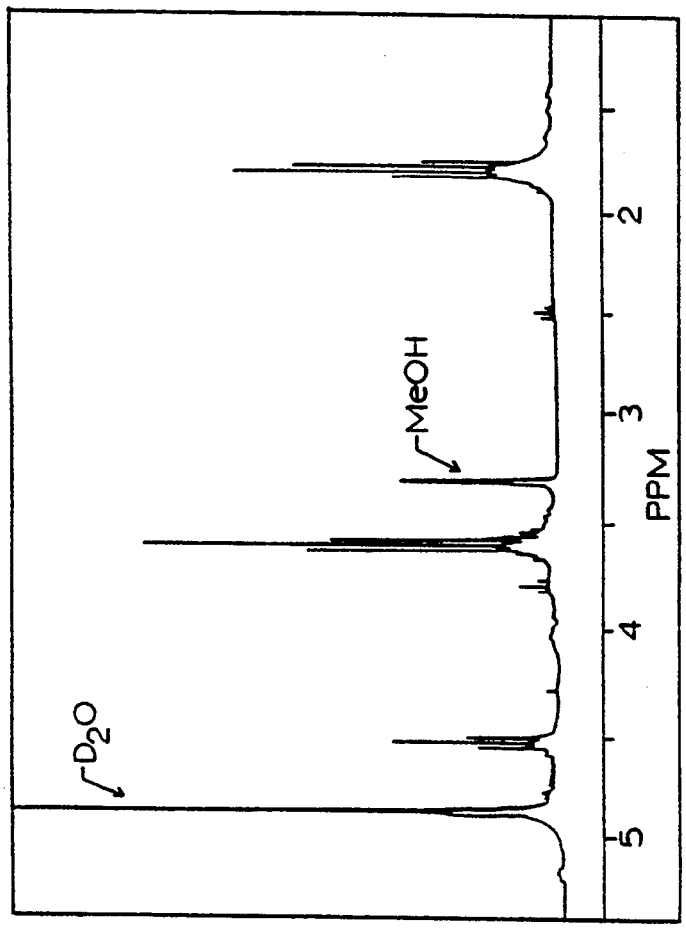
FIG. 21 shows the carbon-13 spectrum of reuterin in deuterated methanol.
Figure 23:
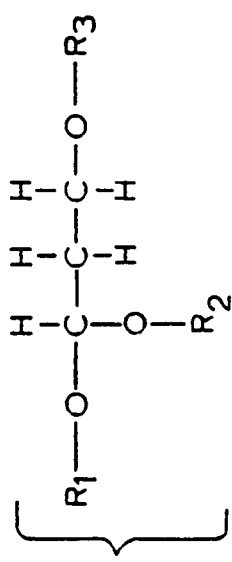
FIG. 23 shows the proposed structure giving rise to the spectra of FIGS. 21 and 22.

The proton spectra determined in deuterated methanol also contained 3 sets of signals occuring around 1.8, 3.6, and 4.5 ppm with a ratio of peak areas of 2:2:1 respectively. The carbon-13 and proton spectra are presented in FIGS. 21 and 22 respectively. A hydrogen ratio of 2:2:1 was suggested due to the relative peak areas of the proton spectra. The proton signal present at 1.8 ppm exists as a quartet and coupling studies indicated its presence as adjacent to the carbons containing protons giving signals occurring at 3.6 and 4.5 ppm. Signals found at 3.6 and 4.5 ppm both exist as triplets and coupling experiments imply only interaction with protons with a signal at 1.8 ppm. The structure shown in FIG. 23 was proposed to correspond to this set of data (including the carbon-13 signal characteristic of disaccharides).

Example XV

Gas chromatography/mass spectrometry of purified reuterin

Trimethylsilylinization was carried out with N,O-bis (Trimethylsilyl) trifluoracetamide (BSTFA) (Pierce Chemical Co., Rockford, Ill.). Two ml of crude reuterin extract were purified by semipreparative chromatography as described above and lyophilized to dryness. One ml of BSTFA was added to the lyophilized reuterin and the silylinization reaction was carried out at ambient temperature. The sample was shaken gently by hand for 5 min until a white precipitate was detected. Just enough HPLC-grade acetonitrile (Fisher Scientific, Raleigh, N.C.) was added to dissolve the precipitate. The sample was then sparged with nitrogen, sealed in a screw top vial and submitted for gas chromatography-mass spectrometry.

A Hewlett Packard 59858 GC/MS (Hewlett Packard, San Jose Calif.) was used in studies on silylated reuterin derivatives. GC conditions were a flow rate of 1.1 ml/min and an injection temperature of 280 degrees C. The program used for analysis consisted of an initial hold period for 3 min at 40 degrees C. with a ramp to 260 degrees C. at 6 degrees C. per min. The column chosen to effect separation was a 15M DBS fused silica capillary column from J & W Scientific (Folsum, Calif.). The mass range was 40–400, an ion source temperature of 200 degrees C., electron energy of 70 eV, electron impact ionization with splitless injection and a split time of 0.8 minutes.

Figure 24:
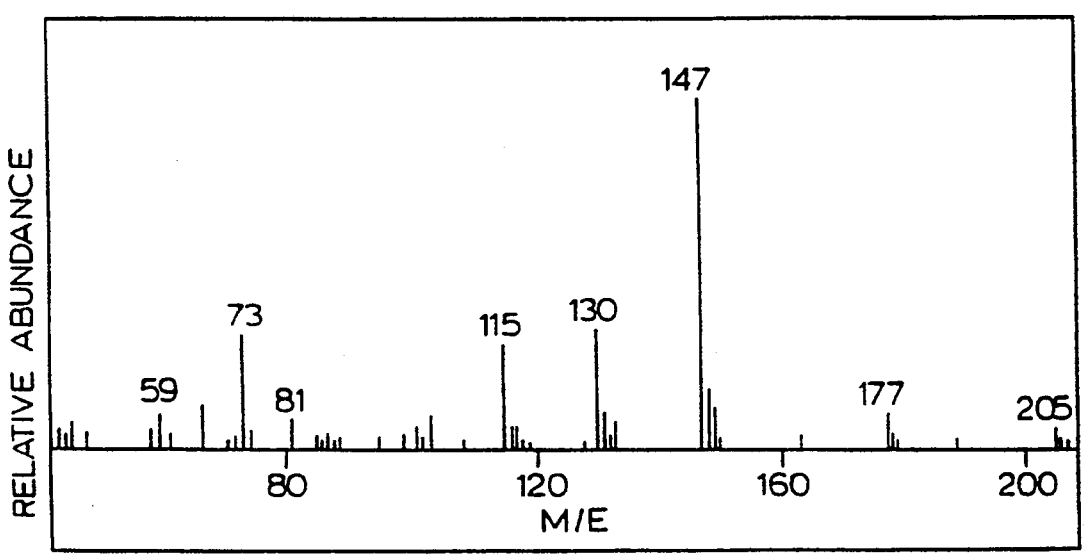
FIG. 24 shows the mass spectra of a trimethylsilyl derivative of reuterin.
Figure 25:
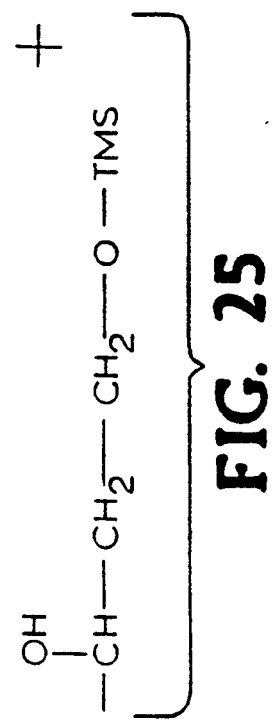
FIG. 25 shows a proposed structure of the fragment of M/E 147.

Reuterin was found to be unstable at the high temperatures present in the GC injector. A stable reuterin derivative was produced upon silanization with BSTFA at ambient temperatures. Chromatography of the derivatized sample produced a complex GC trace (data not shown) but compounds with an apparent molecular weight of 292 (148 plus 2 trimethylsily groups) were found at retention times of between 9 and 14 min. Two peaks were identified as possible isomers (retention time of 11.7 and 13.3 min). A monosilylated derivative was discovered at a retention time of 9.3 minutes and its spectra is presented in FIG. 24. The fragmentation pattern of this compound consists of signals at 205, 177, 163, 147, 130, and 115 M/E units. A reuterin molecule containing one TMS group (ms=220) could undergo loss of a methyl group to produce an M/E value of 205. The fragment at 147 units could conceivably have come from the loss of the TMS group but the pattern of fragments around M/E of 147 indicated the presence of the silicon, carbon, and oxygen natural isotopes. More precisely, the ratio of fragment ions of the 147:148:149 M/E units was 100:16:9, exactly that which would be predicted for a molecular of the composition $C_6H_{15}O_2Si$. This fragment was interpreted as having the structure shown in FIG. 25 and not as a reuterin molecule which had lost the TMS group. Strong signals at M/E 219 and 189 present in the spectra of isomers of derivatized molecules contains 2 TMS groups eluting at 11.7 and 13.3 minutes (data not shown). Illustrations of fragments fulfilling M/E data as well as structural detail as determined by NMR studies are presented in FIG. 27.

Based on the FTIR and LCMS data (FIGS. 16 and 17) of purified reuterin, reuterin was assigned a molecular weight of 148 containing both hydroxyl and aldehydic functionalities. These assumptions fit well with NMR data (samples in $D_2O$). A molecular formula of $C_6H_{12}O_4$ and the structure shown in FIG. 20 were proposed. However, it was clear certain revisions were needed when reuterin NMR studies were carried out in deuterated methanol. Data in this case implied the molecule had only three carbons or was symmetrical about an axis (i.e. 2×3=6). Two possible schemes were proposed to explain this data (FIG. 26).

Scheme A would require the formation of a second hemiacetal bond between the aldehyde and the hydroxyl. The final structure would then exist as an eight membered ring, both halves of which would be symmetrical. This proposed structure does not account well for the carbon signal present at 207 ppm when reuterin is analyzed in deuterated methanol. The structure does fit splitting patterns, proportionality of protons present (2:2:1 ratio of hydrogens on carbons) and chemical shifts observed for the proton spectra in methanol. The hemiacetals would be free to open and reclose in the presence of water (much like sugars undergoing mutarotation over time) and a number of forms could be present at any moment within a reuterin sample. This may lead to the broad peaks observed in the D20 spectra and the lack of accurate integration of signals.

Scheme B would progress through a more structurally favored six membered ring and, coupled with loss of water, would exist as a bicyclic ring in methanol. This molecule would also possess the necessary symmetry to explain the NMP spectra observed in methanol. Furthermore this structure would include a carbon that would give a signal at 104 ppm in a carbon-13 spectra. Chemical shifts and splitting patterns found in the proton spectra (run in D20) would fit the proposed six membered ring structure, and opening of the hemiacetal would present a situation similar to that described above, namely existence of multiple forms of reuterin leading to complicated spectra.

Figure 26:
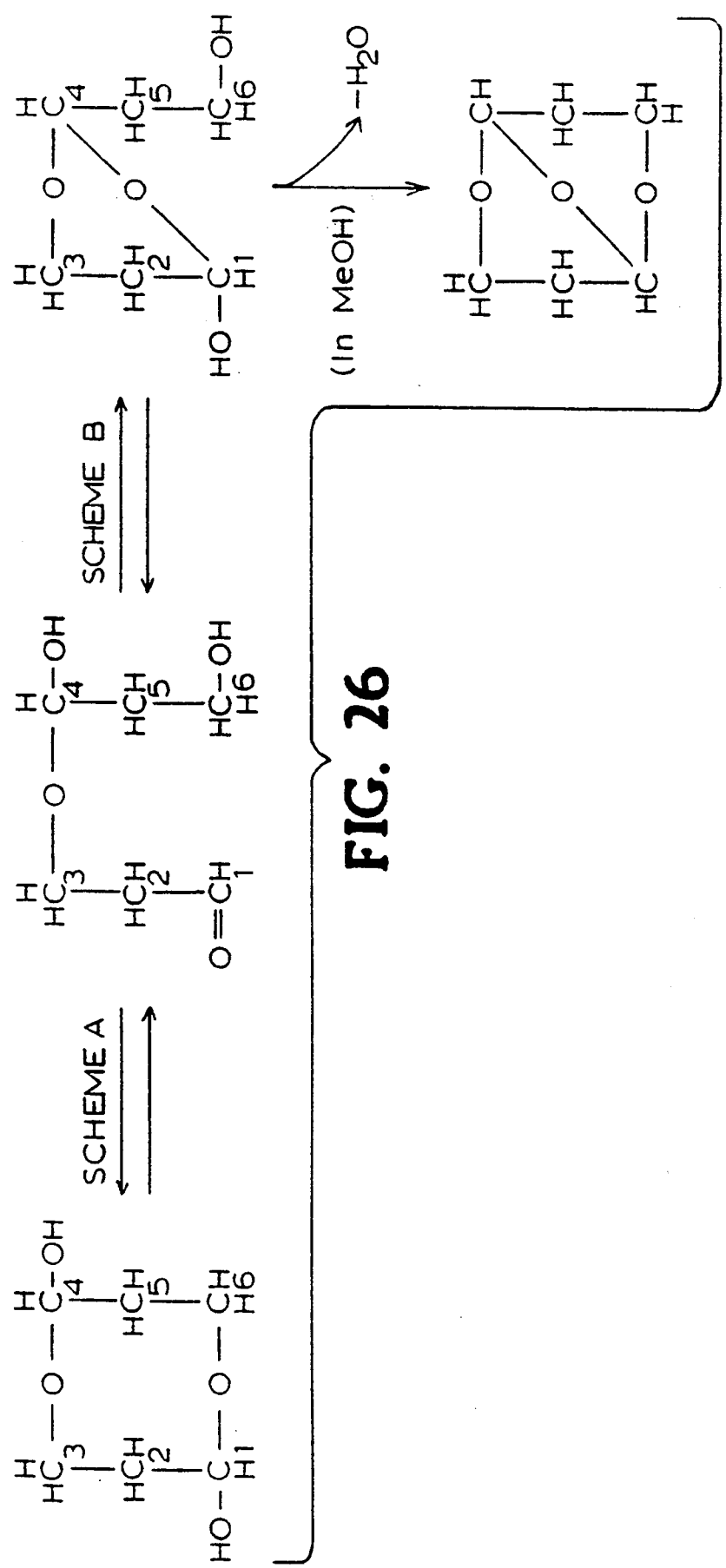
FIG. 26 shows proposed schemes for the reuterin structure.

Further scrutiny of the proton spectrum of reuterin run in D20 (FIG. 19) provides information favoring scheme B (FIG. 26). The straight chain form of reuterin could account for signals present at chemical shifts of 1.6, 2.6, 3.5, 3.7, 5.0, and 9.5 ppm. The area ratio of these signals is clearly not equivalent to the ratio of hydrogen atoms in the molecule (i.e. 1:2:2:1:2:2 for carbon 1-6). If the cyclic form were also present in some equilibrium concentration with straight chain form, protons on carbons 1 and 4 of the ring would be existing in an environment very different from the same protons in the chain form. This would give rise to a new chemical shift for those protons. The environment of protons on carbons 3, 5, and 6 would be relatively constant in either form and the signals would not be expected to shift significantly. As expected the signals from protons on carbons 3, 5, and 6 are broad and show significant deviance from expected area integration values. Development of weak signal patterns around 5 ppm occurs due to protons from predicted ring carbons with two oxygens attached. The presence of two forms of reuterin while in an aqueous solution accounts for the proton spectum observed, whereas slight irreversible degradation of reuterin to 2 molecules of β-hydroxypropionaldehyde would also explain the proton spectra.

Figure 27:
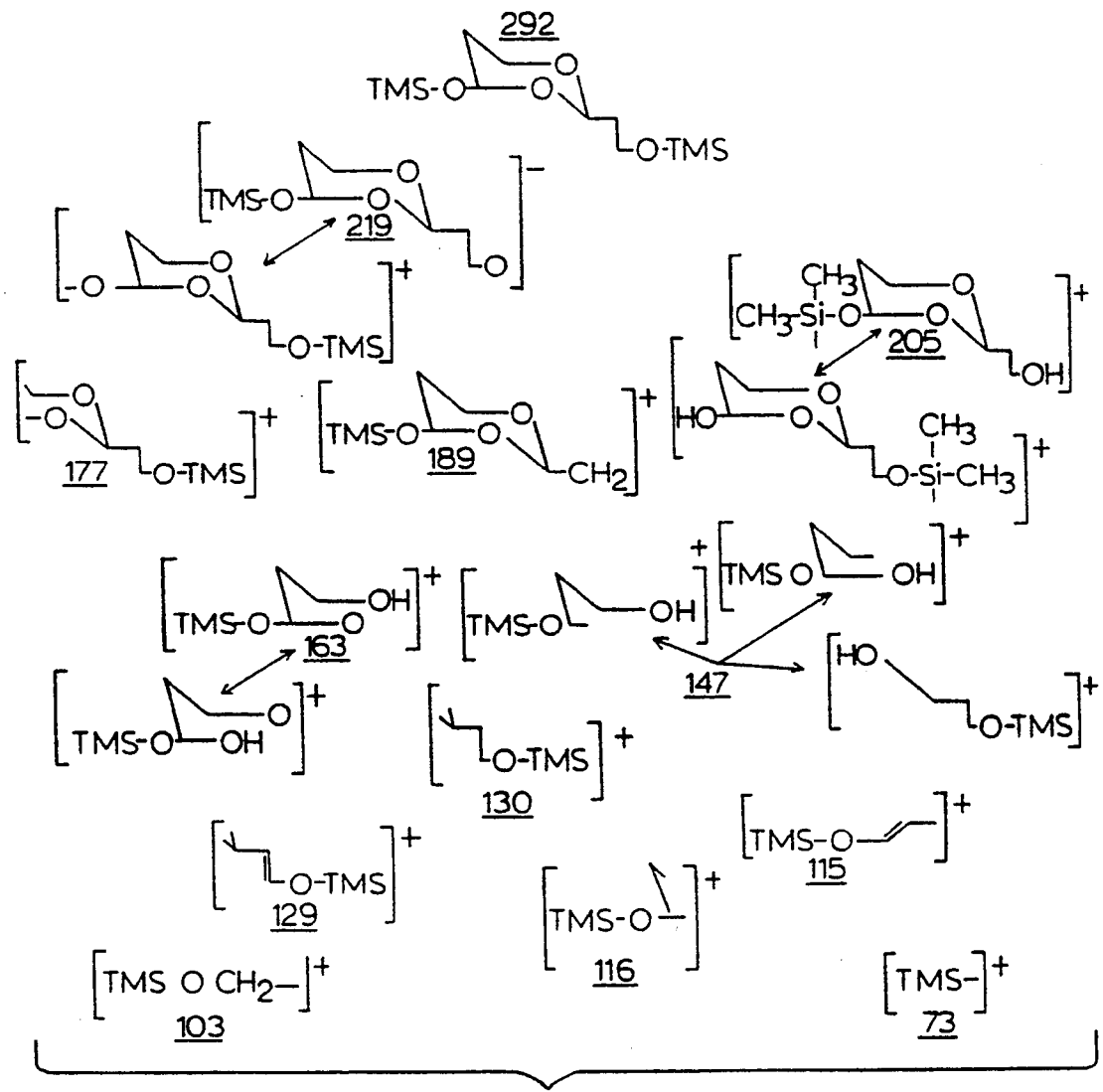
FIG. 27 shows fragments fulfilling M/E data and NMR structures.

The mass spectra obtained from silylated samples provided another level of detail for the structure of reuterin when considered together with data obtained from NMR studies. Signals present at M/E 147 represent fragments which could be predicted from any of the structures shown in schemes A and B (FIG. 26). However, the fragment observed at M/E 177 should not be present in the fragmentation of the eight membered ring or straight chain. Likewise the signal at M/E 163 would not be predicted for these molecules. Fragments of M/E 177 and 163 are possible if the six membered ring is used as the parent molecule. FIG. 27 details the proposed fragmentation of the silyated six membered ring which fits the data produced from GCMS analysis.

All observed M/E signals can be accounted for either as a fragment of the —CH2—CH2—O—TMS tail or as a fragment of the six-membered ring. Furthermore, the fragment of M/E 147 could be formed from a number of different fragmentations, any of which contain three base carbons, an oxygen, and the —O—TMS group. This point is important because the signals from fragments of M/E 147 are strong in the spectra of both predicted isomers (as well as the monosilylated molecule) separated by GC, indicating both isomers yield the same base ring fragmentations (i.e. have similar structure).

Figure 28:
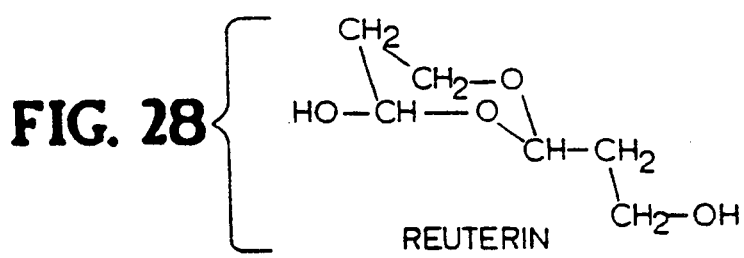
FIG. 28 shows the proposed structure of reuterin as it exists in aqueous solution.

Based on the data compiled to date, the most likely structure of reuterin is that given in FIG. 28. When reuterin is present in an aqueous solution, it must exist in equilibrium with the open chain (based on NMR results) whereas when it is derivatized with BSTFA it is locked exclusively in the cyclic form (GCMS studies). Proton NMR studies of reuterin's structure in acetone coincide with data gathered when reuterin was dissolved in water (data not shown). Further NMR analysis of reuterin dissolved in a 50/50 mixture of methanol water gave results similar to the methanol results presented above. Further analysis of forms predominating in methanol are required to confirm the theory of the bicylic structure. In addition, organic synthesis of reuterin (as its structure is predicted) and subsequent structural analysis is the only absolute method of confirming our structural hypothesis.

Searches in the literature after the structure of reuterin was elucidated revealed that a compound having the same chemical components as reuterin was present in acidic solution upon the hydration of acrolein (29). It also had been previously described as the distillate from a preparation of β-hydroxypropaldehyde with the name 4-hydroxy-2-2'-hydroxyethyl-1:3-dioxan (30).

When 4-hydroxy-2-2'-hydroxyethyl-1:3-dioxan was synthesized in our laboratory as described by Hall (30), it eluted at the same HPLC peak as reuterin and exhibited an idential MIC value as the biologically synthesized reuterin. Therefore, the structure shown in FIG. 27 is that of reuterin.

β-Hydroxypropaldehyde (also called: 3-hydroxypropanal, hydracryaldehyde, β-hydroxypropionaldehyde, 3-hydroxypropan-1-al) is of greater potential value in the solvent or the plasticiser field (Hall, R. H., and Stern, E. S., Journal Chemical Society, Jan.-Mar., 1950 pp. 490-498). It has been confirmed that the dimeric hydroxypropaldehyde (i.e., reuterin or 4-hydroxy-2-2'-hydroxyethyl-1:3-dioxan) and the monomeric β-hydroxypropaldehyde are in equilibrium in solution (Ibid). Therefore, the biological production of reuterin from glycerol by *L. reuteri* constitutes a new process for formation of the monomer (beta-hydroxypropionaldehyde) as well as the dimeric form of this substance.

Figure 12:
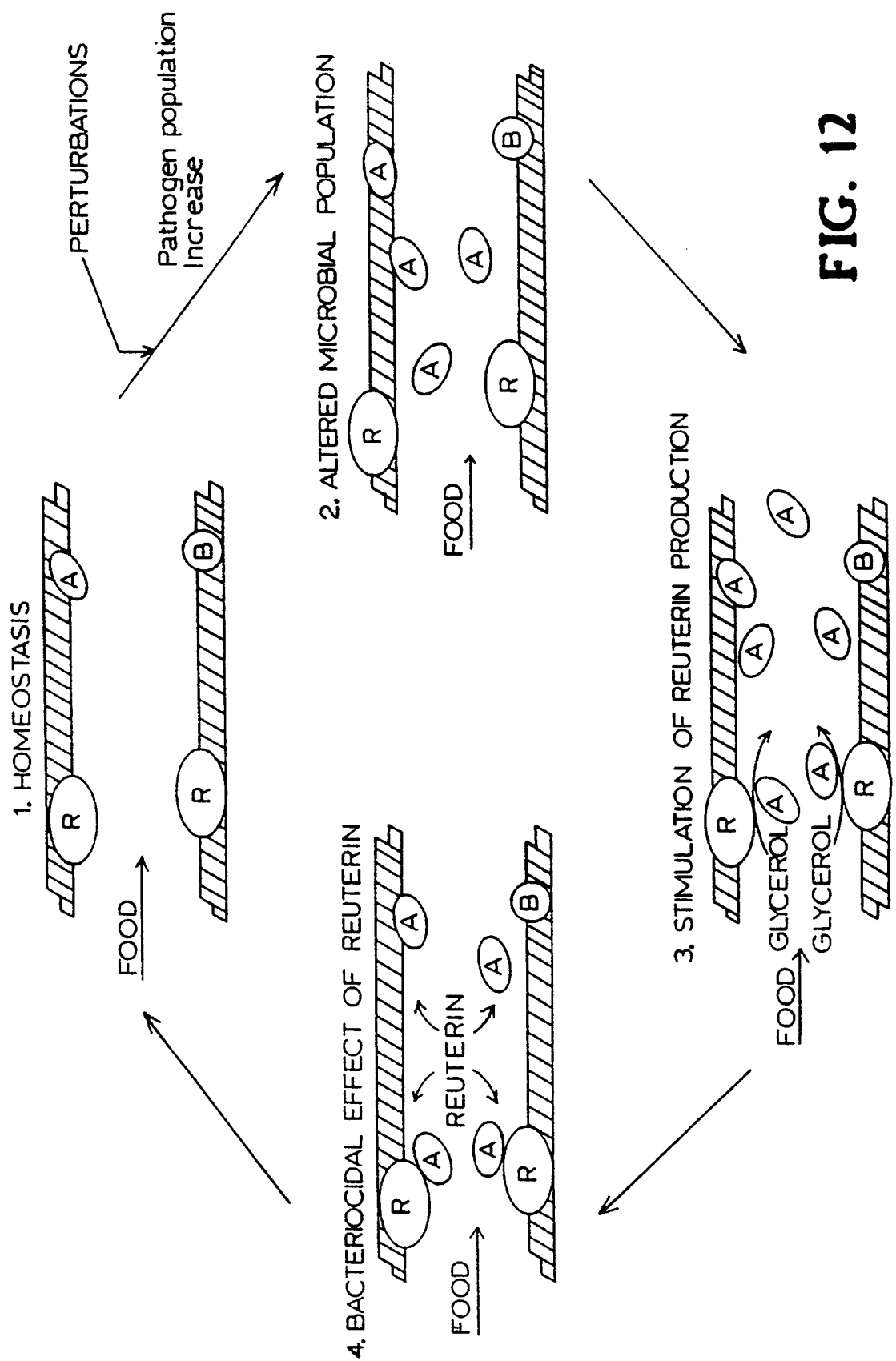
FIG. 12 shows the model of the *L. reuterin*-reuterin system.

The *L. reuteri*-reuterin system: a regulator of enteric microbiotic populations The discovery of this system has led to a new conceptional model describing how microbiotic populations may be regulated in the gastrointestinal tracts of animals. This model is illustrated in the four parts of FIG. 12. In Phase 1, an intestinal segment contains hypothetical bacteria (species A and B) and *L. reuteri* (R) existing in a state of population homeostasis. During phase 2, an increase in the population of a heterologous microbe (organism A in this case) is sensed (by an unknown cell to cell contact mechanism) by the resident *L. reuteri* cells. In phase 3 in the presence of glycerol (or glyceraldehyde), presumably available via pancreatic and/or microbial lipolytic activity, reuterin is synthesized. The bacteriocidal action of reuterin reduces the enteric microbial population in phase 4 and the population homeostasis of phase 1 is restored. This model suggests that the feedback regulation principle which operates so effectively at the metabolic level may function at a cellular level for the maintenance of enteric population homeostasis.

As determined by experimental data given and viewed in light of the feedback model, L. reuteri strain 1063 is deemed best suited of L. reuteri strains to function as a probiotic agent to moderate enteric diseases and enhance feed efficiencies in swine. This conclusion derives from (i) the discovery that strain 1063 produces high levels of reuterin (FIG. 2) and that it is more responsive to heterologous stimulation than the other strains (Table 6), (ii) the fact that strain 1063 was isolated directly from pig small intestines and is therefore a swine host-specific strain, and (iii) the observations that strain 1063 has strong autoaggregation ability and adheres better than other strains tested to pig epithelial cells.

Best Mode for Carrying Out the Invention

Reuterin is obtained by the homologous method wherein L. reuteri cells are grown in still culture at 37 degrees C. in Lactobacillus Carrying Medium with glucose for 24 hours. The cells are harvested by centrifugation and suspended in 250 mM glycerol. After incubation for 6 hours at 37 degrees C. in still culture, the cells are removed by centrifugation and filtration. The reuterin solution is then added to an environment containing reuterin-sensitive microorganisms to kill the microorganisms.

Industrial Applicability

Reuterin has applicability for antiviral, antibacterial, antiparasitic and antifungal use in laboratories. In addition, reuterin may be added to food products to decrease the microbial flora. Reuterin may also be fed to animals to decrease the microbial population in the animal gastrointestinal tract. Lactobacillus reuteri cells may be incubated under conditions conducive for reuterin production to enhance antibacterial activity.

TABLE 1

Reuterin is produced in the presence of glycerol or glyceraldehyde.

| Substitute % added to culture medium | Addition of L. reuteri 1063 | E. coli (CFU/ml) after 6 hours | % Inhibition |
|---|---|---|---|
| Glucose | − | $1.3 \times 10^8$ | 0 |
|  | + | $1.3 \times 10^8$ |  |
| Mannose | − | $7.2 \times 10^7$ | 0 |
|  | + | $9.0 \times 10^7$ |  |
| Fructose | − | $2.1 \times 10^8$ | 0 |
|  | + | $3.0 \times 10^8$ |  |
| Mannitol | − | $2.3 \times 10^8$ | 0 |
|  | + | $2.7 \times 10^8$ |  |
| Sorbitol | − | $2.1 \times 10^8$ | 0 |
|  | + | $1.9 \times 10^8$ |  |
| Gluconate | − | $3.5 \times 10^8$ | 0 |
|  | + | $3.2 \times 10^8$ |  |
| Xylose | − | $6.7 \times 10^7$ | 0 |
|  | + | $6.9 \times 10^7$ |  |
| Ribitol | − | $5.7 \times 10^6$ | 0 |
|  | + | $4.9 \times 10^6$ |  |
| Arabitol | − | $2.7 \times 10^6$ | 0 |
|  | + | $2.9 \times 10^6$ |  |
| Dihydroxyacetone-P | − | $3.4 \times 10^6$ | 0 |
|  | + | $4.1 \times 10^6$ |  |
| β-Glycerol-P | − | $5.1 \times 10^6$ | 0 |
|  | + | $6.5 \times 10^6$ |  |
| Glycerol | − | $1.2 \times 10^7$ | 99 |
|  | + | $5.5 \times 10^4$ |  |
| Glyceraldehyde | − | $2.8 \times 10^6$ | 99 |
|  | + | $3.2 \times 10^4$ |  |

TABLE 2

Reuterin is found in the culture fluid after removal of cells by centrifugation.

| Substrates present in the culture medium | Growth of E. coli presence of centrifuged culture medium CFU/ml after 6 hours | % Inhibition |
|---|---|---|
| Pyruvate | $4.1 \times 10^9$ | 0 |
| Phosphoenolpyruvate | $3.7 \times 10^9$ | 0 |
| Phosphoglycerate | $3.3 \times 10^9$ | 0 |
| β-Glycerol-P | $3.2 \times 10^9$ | 0 |
| Dihydroxyacetone-P | $3.7 \times 10^9$ | 0 |
| Glycerol | $4.5 \times 10^5$ | 99.9 |
| Glyceraldehyde | $6.1 \times 10^5$ | 98.9 |
| No Substrate | $3.6 \times 10^9$ | 0 |

TABLE 3

Production of reuterin under different cultural conditions.

| | | | Reuterin Units Produced | | | |
|---|---|---|---|---|---|---|
| Time (Hr) | Complete System | Minus E. coli | E. coli in dialysis tubing In | Out | E. coli culture +1063 | spent fluid −1063 |
| 0 | 0 | 0 | 0 | 0 | 0 | 0 |
| 1 | 16 | — | — | 1 | 1 | — |
| 2 | 24 | — | — | 4 | 4 | — |
| 3 | 32 | — | — | 6 | 4 | — |
| 4 | 32 | — | — | 8 | 6 | — |
| 5 | 32 | — | — | 8 | 8 | — |
| 6 | 32 | 8 | 4 | 8 | 8 | 0 |

TABLE 4

Effect of culture medium and E. coli viability on reuterin production by L. reuteri 1063.

| | Reuterin Units | | | |
|---|---|---|---|---|
| Culture conditions | E. coli alone | L. reuteri 1063 alone | E. coli plus L. reutri 1063 | Heat-killed E. coli plus L. reuteri 1063 |
| Complete Medium | 0 | 6 | 48 | 6 |
| Glycerol-Water | 0 | 6 | 6 | 2 |

TABLE 5

Homologous and heterologous production of reuterin by three strains of L. reuteri at varying concentrations.

| | Units of reuterin produced (6 hr incubation) | | | | | |
|---|---|---|---|---|---|---|
| L. reuteri CFU per ml | strain 1063 E. coli | | strain 23272 E. coli | | strain 20016 E. coli | |
|  | (−) | (+) | (−) | (+) | (−) | (+) |
| $1.2 \times 10^{10}$ | 96 | — | — | — | — | — |
| $4.0 \times 10^9$ | 48 | — | — | — | — | — |
| $1.3 \times 10^9$ | 24 | — | — | — | — | — |
| $4.4 \times 10^8$ | 4 | — | — | — | — | — |
| $2.0 \times 10^8$ | 0 | 96 | 4 | 48 | 48 | 96 |
| $7.0 \times 10^7$ | 0 | 48 | 2 | 32 | 6 | 48 |
| $2.3 \times 10^7$ | 0 | 32 | 0 | 16 | 6 | 32 |
| $7.6 \times 10^6$ | 0 | 12 | 0 | 6 | 3 | 12 |

TABLE 5-continued

Homologous and heterologous production of reuterin by three strains of L. reuteri at varying concentrations.

| L. reuteri CFU per ml | Units of reuterin produced (6 hr incubation) | | | | | |
|---|---|---|---|---|---|---|
| | strain 1063 E. coli | | strain 23272 E. coli | | strain 20016 E. coli | |
| | (−) | (+) | (−) | (+) | (−) | (+) |
| 2.5 × 10$^6$ | 0 | 0 | 0 | 0 | 0 | 1 |

+:E. coli = Co-incubation of 20 CFU E. coli per CFU L. reuteri
−: No E. coli

TABLE 6

Sensitivity to reuterin and stimulaton of reuterin production by various bacterial species.

| Bacterial strains tested | Sensitivity to reuterin | Stimulation of reuterin produced by indicated strains in glycerol medium produced by indicated strains in glycerol medium Reuterin units |
|---|---|---|
| I. Gram negative bacteria: | | |
| Escherichia coli K12 (wild type) | VS | 32 |
| Escherichia coli 431 (swine enteropathogen) | VS | 64 |
| Escherichia coli 73 (swine enteropathogen) | VS | 64 |
| Escherichia coli P55 (swine enteropathogen) | VS | 64 |
| Escherichia coli 263 (swine enteropathogen) | VS | — |
| Escherichia coli P159 (swine enteropathogen) | VS | — |
| Escherichia coli CII-P7 (swine enteropathogen) | VS | — |
| Salmonella typhimurium | VS | 64 |
| Shigella species | VS | 64 |
| Proteus species | VS | 32 |
| Pseudomonas fluorescens | VS | 64 |
| II. Gram positive bacteria: | | |
| Staphylococcus epidermidis | VS | 32 |
| Streptococcus cremoris | VS | 8 |
| Clostridium sporogenes | S | 8 |
| Bacillus megaterium | S | 12 |
| Pediococcus cerevisiae | S | 8 |
| Leuconostoc mesenteroides | S | 8 |
| III. Yeast: | | |
| Saccharomyces cerevisiae | S | 12 |

VS = very sensitive; S = sensitive

TABLE 7

Inhibition of the B1 subunit of ribonucleotide reductase and inhibition of thioredoxin by reuterin

| Enzyme/Subunit | Reuterin, ul/nmole protein to produce 50% inhibition |
|---|---|
| B1 | 53 |
| B2 | 555 |
| Thioredoxin | 34 |
| Thioredoxin reductase | >5000 |

TABLE 8

| | NH$_3$ (mg per 100 g) | Log CFU bacteria per g | | |
|---|---|---|---|---|
| | | Pseudomonads (kings agar) | LAB total | LAB hetero |
| Control | 164 | 9.5 | <5.0 | <4.0 |
| glycerol | 64 | 9.4 | 5.5 | 5.1 |
| 1068 | 36 | 8.4 | 8.5 | 8.6 |
| 1063 | 28 | 6.7 | 7.7 | 7.8 |

REFERENCES

1. Kandler, O., et al., Zbl. Bakt. Hgg., I. Abt. orig. Cl, 264–269 (1980).
2. Bergey's Manual of Systematic Bacteriology, Vol. 2. Ed. by P. H. A. Sneath, N. S. Mair, M. E. Sharpe and J. G. Holt, Williams and Wilkins, Baltimore (1986).
3. Sandine, W. E., et al., J. Milk Food Technol., 35:691 (1972).
4. Goldin, B. R., et al., J. Natl. Cancer Institute, 64:255 (1980).
5. Goldin, B. R., et al., Development in Industrial Microbiology, 25:139 (1984).
6. Goldin, B. R., et al., Am. J. Clin. Nutr., 39:756 (1984).
7. Gilliland, S. E., et al., Appl. Environ. Microbiol., 49:377 (1985).
8. Schutz, H., et al., System. Appl. Microbiol., 5:169 (1984).
9. Sobolov, M., et al., J. Bacteriol., 79:261 (1960).
10. Smiley, K. L., et al., Arch Biochem. Biophys., 97:538 (1962).
11. Metchnikoff, Prolongation of Life, G. P. Putnam's Sons, New York, N.Y., 1970.
12. Klaenhammer, T. R., et al., J. Dairy Science, 65:1339 (1982).
13. Dahiya, R. S., et al., J. Dairy Science, 51:1568 (1968).
14. Gilliland, S. E., et al., J. Milk Food Technol., 35:307 (1972).
15. Pinheiro, A. J. R., et al., J. Dairy Science, 57:183 (1968).
16. Price, R. J., et al., J. Milk Food Technol., 33:18 (1970).
17. Sorrels, K. M., et al., J. Dairy Science, 53:239 (1970).
18. Talon, R. J., et al., Zentralbl. Bakteriol. Abt. Orig. B170:133 (1980).
19. Gilliland, S. E., et al., J. Food Pretection, 40:820 (1977).
20. Tramer, J., et al., Nature, 211:204 (1966).
21. Shahani, K. M., et al., Cult. Dairy Prod. J., 12:8 (1977).
22. Shahani, K. M., et al., Cult. Dairy Prod. J., 11:14 (1976).
23. Reddy, G. V., et al., J. Dairy Science, 54:748 (1971).
24. Hamdan, I. Y., et al., J. Antibiotics, 27:631 (1974).
25. Hamdan, I. Y., et al., Cult Dairy Prod. J., 10:10 (1975).
26. Spillman, H., et al., Milchwissenschaft, 33:148 (1978).
27. Vincent, J. G., et al., J. Bacteriol., 78:477 (1959).
28. Sandine, W. E., J. Food Protection, 42:259 (1979).
29. Nielsen, A. T., et al., Polish Journal of Chemstry, 55:1393 (1981).
30. Hall, R. H., et al., J. Chem. Society, 1950:490 (1950).

I claim:

1. A method for determining the presence of the antibiotic β-hydroxypropionaldehyde as a detectable end-product in an aqueous solution of Lactobacillus reuteri cells comprising the steps of:
   (a) placing Lactobacillus reuteri cells in an aqueous solution containing a compound selected from the group consisting of glycerol and glyceraldehyde as the carbon and energy source at a concentration of about 20–500 mM, and incubating said cells under anaerobic conditions;
   (b) separating the Lactobacillus reuteri cells from a sample of the solution;
   (c) analyzing the sample using high performance liquid chromatography;
   (d) eluting the sample; and (e) determining the presence of a peak intermediate in elution time to those of 1,3-propanediol and glycerol which is indicative of the presence of β-hydroxypropionaldehyde in the sample.

2. A method for identifying *Lactobacillus reuteri* isolates that produce the antibiotic β-hydroxypropionaldehyde as a detectable end-product, which comprises the steps of:
   (a) inoculating a suspension of microorganisms from an animal source on a solid Lactobacillus growth medium made to be highly selectively for Lactobacillus by addition of sodium acetate and adjustment of the medium pH to 5.5;
   (b) incubating said inoculated growth medium under conditions that promote growth of Lactobacillus colonies;
   (c) overlaying the inoculated growth medium and colonies with a liquified semisolid mixture containing a suspension of a living test microroganism and a compound selected from the group consisting of glycerol and glyceraldehyde as the carbon and energy source at a concentration of about 20–500 mM;
   (d) incubating the overlaid inoculated medium under anaerobic conditions; and
   (e) identifying in situ *Lactobacillus reuteri* colonies that produce β-hydroxypropionaldehyde by detecting zones of growth inhibition in the test microorganism surrounding said colonies.

3. The method for identifying *Lactobacillus reuteri* isolates of claim 2 wherein the carbon source is glycerol and the living test microorganism is *Lactobacillus plantarum*.

4. The method for identifying *Lactobacillus reuteri* isolates of claim 2 wherein the conditions of incubation comprise an incubation temperature of 37 degrees C. for 48 hours.

* * * * *

UNITED STATES PATENT AND TRADEMARK OFFICE
CERTIFICATE OF CORRECTION

PATENT NO.   : 5,352,586
DATED        : October 4, 1994
INVENTOR(S)  : Walter J. Dobrogosz and Sven E. Lindgren It is certified that error appears in the above-indentified patent and that said Letters Patent is hereby corrected as shown below:

Column 3, line 57, "pro teases" should be --proteases--

Column 6, line 14, "quanine" should be --guanine--

Column 7, line 5, "productions" should be --production--

Column 11, line 11, "diluations" should be --dilutions--

Column 11, line 39, the symbol should be a filled in square

Column 11, line 40, the blank space should contain an open diamond

Column 12, line 9, "psuedomonads" should be --pseudomonads--

Column 12, line 21, "psuedomonads" should be --pseudomonads--

Column 14, line 34, "verus" should be --versus--

Signed and Sealed this

Twenty-eight Day of February, 1995

Attest:

BRUCE LEHMAN

Attesting Officer    Commissioner of Patents and Trademarks